United States Patent
Kim et al.

(10) Patent No.: US 11,400,303 B2
(45) Date of Patent: Aug. 2, 2022

(54) DETECTING WALKING IN A WEARABLE CARDIOVERTER DEFIBRILLATOR SYSTEM

(71) Applicant: WEST AFFUM HOLDINGS DAC, Dublin (IE)

(72) Inventors: Jaeho Kim, Redmond, WA (US); Joseph L. Sullivan, Kirkland, WA (US); Robert P. Marx, Redmond, WA (US)

(73) Assignee: West Affum Holdings Corp., Grand Cayman (KY)

( * ) Notice: Subject to any disclaimer, the term of this patent is extended or adjusted under 35 U.S.C. 154(b) by 626 days.

(21) Appl. No.: 16/158,174

(22) Filed: Oct. 11, 2018

(65) Prior Publication Data
US 2019/0209853 A1    Jul. 11, 2019

Related U.S. Application Data

(63) Continuation-in-part of application No. 15/863,551, filed on Jan. 5, 2018, now Pat. No. 11,083,906.

(Continued)

(51) Int. Cl.
*A61N 1/39* (2006.01)
*A61B 5/11* (2006.01)
(Continued)

(52) U.S. Cl.
CPC .............. *A61N 1/3987* (2013.01); *A61B 5/11* (2013.01); *A61B 5/1123* (2013.01); *A61B 5/282* (2021.01);
(Continued)

(58) Field of Classification Search
CPC . A61B 5/04018; A61B 5/0432; A61B 5/6805; A61B 2562/0219; A61B 5/11;
(Continued)

(56) References Cited

U.S. PATENT DOCUMENTS 3,724,355 A    4/1973  Busch et al.
3,724,455 A    4/1973  Unger
(Continued)

FOREIGN PATENT DOCUMENTS

DE    2005060985 A2    6/2007
EP       2305110 A1    4/2011
(Continued)

OTHER PUBLICATIONS

Klein, H.U., et al., "Risk Stratification for Implantable Cardioverter Defibrillator Therapy: The Role of the Wearable Cardioverter-Defibrillator," Clinical Update, European Heart Journal, May 31, 2013, 14 pages, European Society of Cardiology, France.

(Continued)

*Primary Examiner* — Amanda K Hulbert
(74) *Attorney, Agent, or Firm* — Christensen O'Connor Johnson Kindness PLLC

(57) ABSTRACT

A wearable medical includes a walking detector module with a motion sensor that is configured to detect when the patient is walking or running. In embodiments, a parameter (referred to herein as a "Bouncy" parameter) is determined from Y-axis acceleration measurements. In some embodiments, the Bouncy parameter is a measurement of the AC component of the Y-axis accelerometer signal. This detection can be used by the medical device to determine how and/or whether to provide treatment to the patient wearing the medical device. For example, when used in a WCD, the walking detector can prevent "false alarms" because a walking patient is generally conscious and not in need of a shock.

11 Claims, 19 Drawing Sheets

Related U.S. Application Data

(60) Provisional application No. 62/717,490, filed on Aug. 10, 2018.

(51) Int. Cl.
  *A61B 5/00* (2006.01)
  *A61B 5/282* (2021.01)
  *A61N 1/04* (2006.01)
  *A61N 1/365* (2006.01)
  *A61B 5/361* (2021.01)
  *A61B 5/363* (2021.01)

(52) U.S. Cl.
  CPC .......... *A61B 5/6802* (2013.01); *A61B 5/6823* (2013.01); *A61B 5/7257* (2013.01); *A61B 5/746* (2013.01); *A61N 1/39046* (2017.08); *A61N 1/3993* (2013.01); *A61B 5/361* (2021.01); *A61B 5/363* (2021.01); *A61B 5/6805* (2013.01); *A61B 5/6831* (2013.01); *A61B 2562/0219* (2013.01); *A61N 1/046* (2013.01); *A61N 1/0484* (2013.01); *A61N 1/36542* (2013.01); *A61N 1/3925* (2013.01)

(58) Field of Classification Search
  CPC ....... A61B 5/1123; A61B 5/282; A61B 5/361; A61B 5/363; A61B 5/6802; A61B 5/6823; A61B 5/6831; A61B 5/7257; A61B 5/746; A61N 1/0484; A61N 1/3904; A61N 1/3925; A61N 1/3968; A61N 1/046; A61N 1/36542; A61N 1/39046; A61N 1/3987; A61N 1/3993
  See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,658,292 B2 * | 12/2003 | Kroll .................. A61N 1/36585 607/19 |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,148,483 B1 | 9/2015 | Molettiere et al. |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 * | 11/2010 | Donnelly ............. A61N 1/3904 607/6 |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |

(56) References Cited

U.S. PATENT DOCUMENTS

| | | |
|---|---|---|
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0065976 A1 | 3/2014 | Jones et al. |
| 2014/0070957 A1 | 3/2014 | Longinotti-Buitoni et al. |
| 2014/0163663 A1 | 6/2014 | Poddar et al. |
| 2014/0188638 A1 | 7/2014 | Jones et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | |
|---|---|---|
| JP | 4320257 A | 3/2005 |
| JP | 5963767 A | 1/2014 |
| JP | 2014526282 A | 10/2014 |
| WO | 98/039061 A2 | 9/1998 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Lifecor LifeVest System Model WCD 3100 Operator's Manual, 2006, Zoll Lifecor Corporation, Pittsburgh, PA, PN 20B0040 Rev FI, 48 pages.

LifeVest Model 4000 Patient Manual, 108 pages, Zoll, Pittsburgh, PA, PN 20B0047 Rev B.

Heartstart MRx and XL AED Algorithm—Application Note, Jul. 2001, Edition 2, Philips Healthcare, USA, 10 pages.

The LifeVest Network/Patient Data Management System, Zoll, 2015, 20C0503 Rev A, 4 pages.

Pagan-Carlo, et al., "Encircling Overlapping Multipulse Shock Waveforms for Transthoracic Defibrillation," JACC Journals, Dec. 1998, vol. 32 Issue 7, p. 2065-2071.

Heartstart MRx and XL AED Algorithm—Application Note, Jul. 2001, Edition 2 Philips Healthcare, USA.

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

ADXL346 Data Sheet, Analog Devices, Inc., Rev. C, Nov. 2016, 41 pages.

Activity Monitoring Solution, Analog Devices, Inc., 4 pages.

Scarlett, "Enhancing the Performance of Pedometers Using a Single Accelerometer," AN-900 Application Note, Analog Devices, Inc., Rev. 0, 16 pages.

Valero et al., ADXL346 Demo—Pedometer, "Hip Pedometer Algorithm," V2.0, Jul. 8, 2011, 16 pages.

* cited by examiner

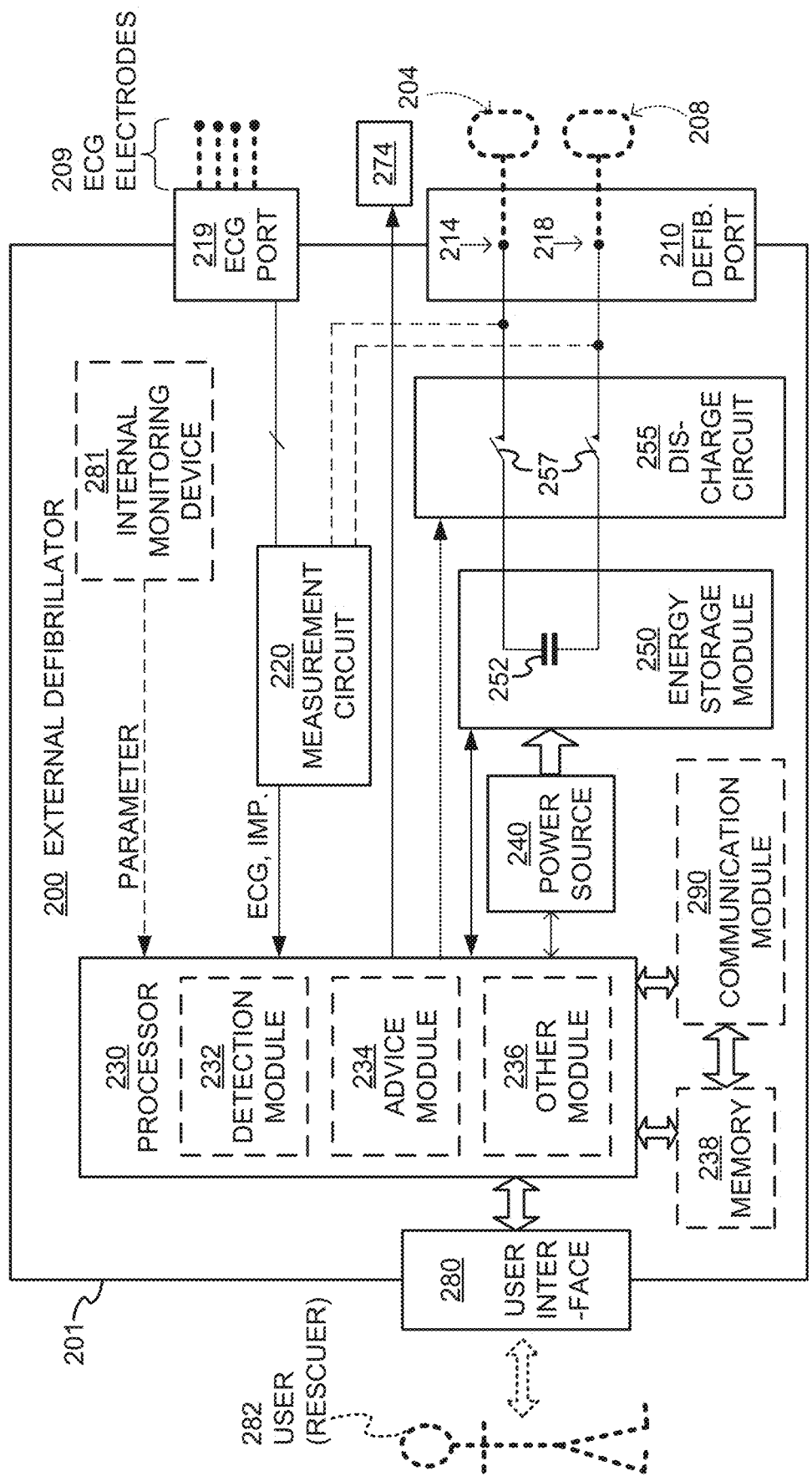
FIG. 2 SAMPLE COMPONENTS OF EXTERNAL DEFIBRILLATOR

RELEVANT COMPONENTS OF EXTERNAL DEFIBRILLATOR WITH WALKING DETECTION

//DETECTING WALKING IN A WEARABLE CARDIOVERTER DEFIBRILLATOR SYSTEM

CROSS REFERENCE TO RELATED PATENT APPLICATIONS

This patent application is a continuation-in-part of U.S. patent application Ser. No. 15/863,551 filed Jan. 5, 2018, titled WEARABLE CARDIOVERTER DEFIBRILLATOR HAVING ADJUSTABLE ALARM TIME, which is incorporated by reference herein in its entirety. This patent application claims benefit of U.S. Provisional Patent Application No. 62/717,490 filed Aug. 8, 2018, titled DETECTING WALKING IN A WEARABLE CARDIOVERTER DEFIBRILLATOR (WCD) SYSTEM and U.S. Provisional Patent Application No. 62/446,820 filed Jan. 16, 2017, titled DETECTING WALKING IN A WEARABLE CARDIOVERTER DEFIBRILLATOR (WCD) SYSTEM and is incorporated by reference herein in their entirety.

BACKGROUND

When people suffer from some types of arrhythmias, the results may be that blood flow to various parts of the body is reduced, and some arrhythmias may even result in sudden cardiac arrest (SCA), which can lead to death very quickly unless treated immediately.

People with an increased risk of SCA often receive an implantable cardioverter defibrillator (ICD). If certain types of heart arrhythmias are detected, then the ICD delivers an electric shock through the heart. However, prior to receiving the ICD, many of these patients receive a wearable cardioverter defibrillator (WCD) system. A WCD system typically includes a harness, vest, or other garment that the patient wears, as well as electronic components, such as a defibrillator and external electrodes, coupled to the garment. When the patient wears the WCD system, the external electrodes make electrical contact with the patient's skin to help determine the patient's electrocardiogram (ECG). If a shockable heart arrhythmia is detected, the defibrillator may then deliver an appropriate shock through the patient's body.

When a VF rhythm is detected, a WCD sends out an alarm to warn the patient and bystanders that a shock is about to occur. If the patient is conscious, typical WCDs do not want the shock to be delivered—in such "false alarm" cases the conscious patient is instructed to divert or abort the shock via a user interface or button provided on the WCD. If there is no response from the patient to divert the therapy, a patient is assumed to be hemodynamically unstable and unconscious and the WCD delivers a needed shock therapy.

BRIEF DESCRIPTION OF THE DRAWINGS

FIG. 2 is a block diagram illustrating sample components of an external defibrillator, such as the one belonging in the system of FIG. 1, according to embodiments of the disclosure.

DESCRIPTION

A wearable cardioverter defibrillator (WCD) system made according to embodiments has several components. These components can be provided separately as modules that can be interconnected, or can be combined with other components, etc.

Figure 1:
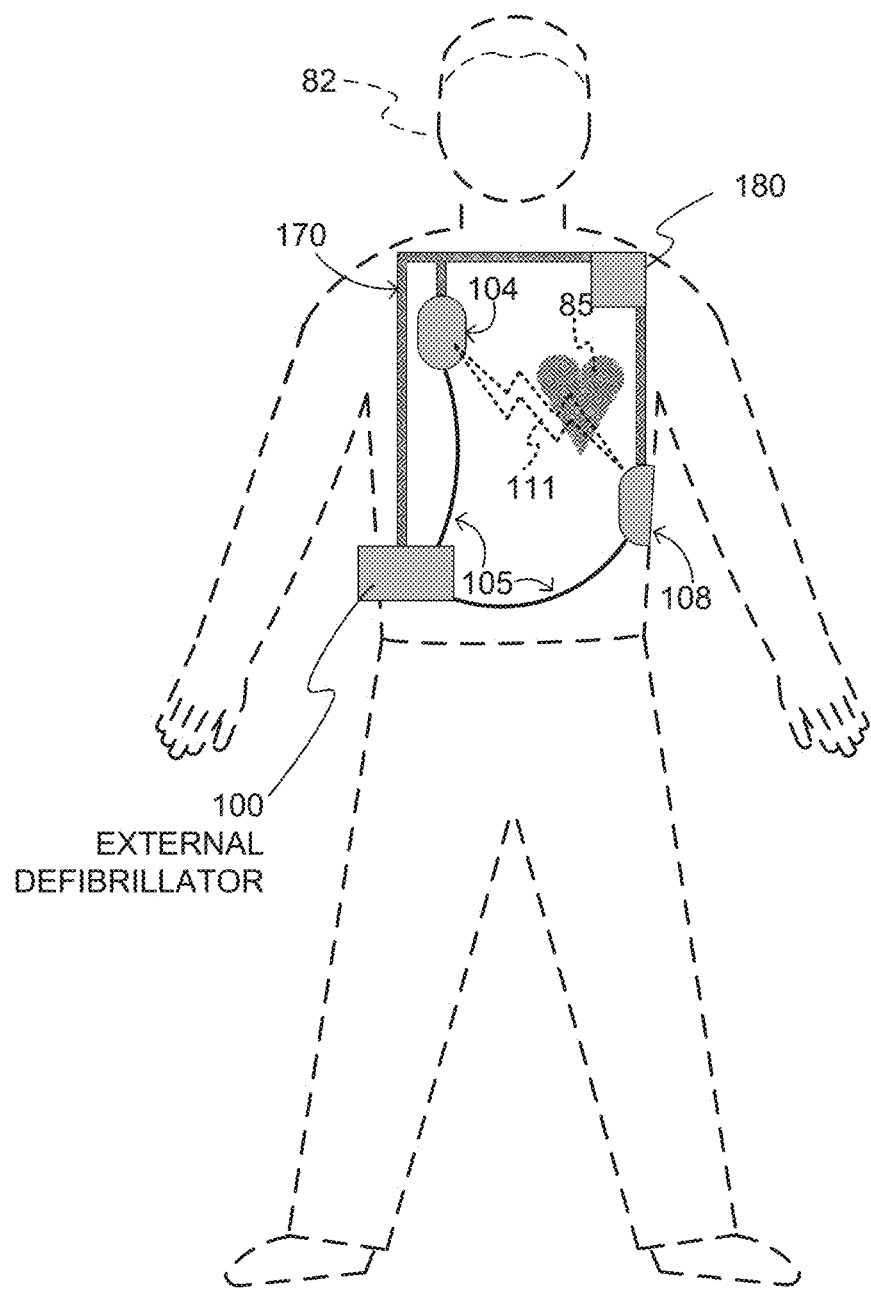
FIG. 1 is a diagram of components of a sample WCD system, according to embodiments of the disclosure.

FIG. 1 depicts a patient 82. Patient 82 may also be referred to as a person and/or wearer, since that patient wears components of the WCD system.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways in different embodiments. For example, in one embodiment implemented in a single component or a combination of multiple components. In embodiments, support structure 170 could include a vest, a half-vest, a garment, etc. In such embodiments, such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US 2017/0056682 A1, which is incorporated herein by reference. After review of this disclosure, in such embodiments, the person skilled in the art will recognize that additional components of the WCD system can be in the housing of a support structure instead of attached externally to the support structure, for example as described in the 2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as shock, defibrillation shock, therapy or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, some embodiments of external defibrillator 100 can initiate defibrillation (or hold-off defibrillation) based on a variety of inputs, with ECG merely being one of them.

Accordingly, in some embodiments of external defibrillator 100, signals such as physiological signals containing physiological data are obtained from patient 82. While the patient may be considered also a "user" of the WCD system, in some embodiments, for example, a user of the WCD may be a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 280 can be made in many ways according to various embodiments. User interface 280 may include output devices, which can be visual, audible or tactile, for communicating to a user by outputting images, sounds or vibrations. Images, sounds, vibrations, and anything that can be perceived by user 282 can also be called human perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which monitoring device can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. It will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally, a WCD system according to embodiments also includes a fluid that it can deploy automatically between the electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from processor 230 that is described more fully later in this document.

In some embodiments, defibrillator 200 also includes a measurement circuit 220, as one or more of its sensors or transducers. Measurement circuit 220 senses one or more electrical physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition, the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module implemented using software includes a set of the instructions so as to offer or fulfill a particular functionality. Embodiments of modules and the functionality delivered are not limited by the embodiments described in this document.

Processor 230 can be considered to have one or more modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232.

There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Various embodiments of processor 230 can include additional modules, such as other module 236, for other functions. In addition, if internal monitoring device 281 is indeed provided, it may be operated in part by processor 230, etc.

Embodiments of defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. Module 290 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on. Defibrillator 200 in some embodiments can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 2A:
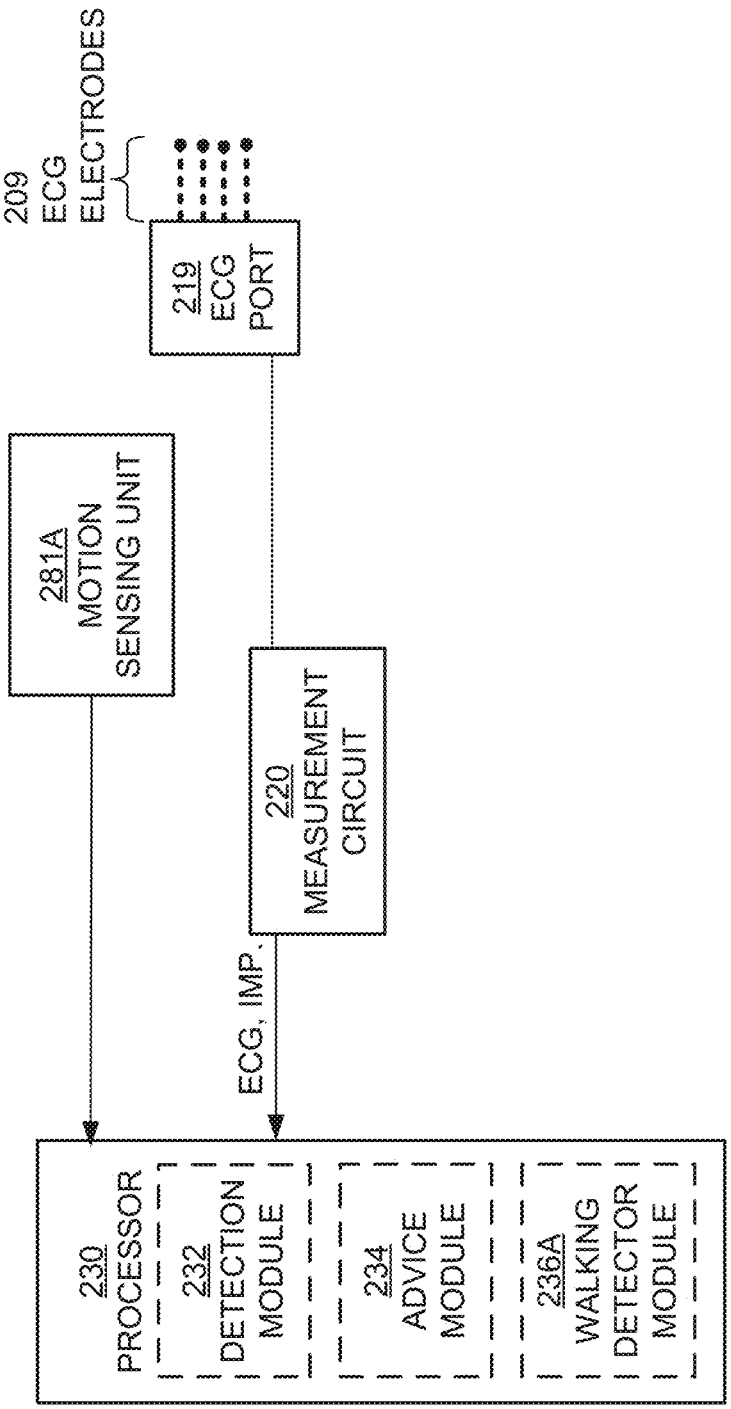
FIG. 2A is a partial block diagram illustrating components used for walking detection in an external defibrillator, according to embodiments of the disclosure.

In some embodiments, other module 236 includes a walking detector module and internal monitoring device 281 includes a motion detector. FIG. 2A illustrates an embodiment of an external defibrillator 201A similar to external defibrillator 201 illustrated in FIG. 2, but with the other module 236 (FIG. 2) being implemented with a walking detector 236A, and internal monitoring device 281 (FIG. 2) being implemented with a motion sensor 281A. External defibrillator 201A includes the other elements shown in FIG. 2, but are omitted in FIG. 2A to more clearly describe the elements used to implement walking detection in a WCD. Some embodiments of external defibrillator 201A illustrated in FIG. 2A may be advantageously used to prevent "false alarms" because a walking patient is generally conscious and not in need of a shock, as described below. For example, in some embodiments, in response to detecting that the patient is walking, the WCD is configured to inhibit or delay or prevent the following actions that would otherwise occur when a shockable rhythm is detected. In other embodiments, the WCD is also configured to inhibit or delay or prevent the additional action of opening a record that is stored in the WCD and/or remotely. In some embodiments, such records are created for storage of waveform and other data surrounding treatment and nontreatment related events. Some records are available for external clients. For example in some embodiments, when VT/VF is detected and sustained for 15 seconds, a record is opened and ECG waveforms with other related information are stored for later review by external users. Some records include one or more of: ECG waveforms, battery status, change in ECG electrode contact, errors states detected in the WCD, ECG channel selection (s), gain settings, impedance measurements, patient user interface activity, changes in arrhythmia detections, therapy deliveries, energy delivery, audio recordings during episodes, etc.

Such embodiments can be advantageous because regardless of the heart rates and other patient data that is detected, opening or creating such a record when the patient is walking would consume resources such as, for example, battery, memory, processing power, and clinician review of the patient record.

In embodiments, motion sensing unit 281 provides one or more output signals to processor 230. These output signals are indicative of the patient's motion. In some embodiments, the motion sensing unit includes a three-axis accelerometer as described below in conjunction with FIGS. 3 and 4. In other embodiments, other types of motion sensors can be used such as force, pressure, inertial, velocity, and position sensors. For example, the force sensors used in products available from Sensoria, Inc., Redmond, Wash. can be used in some embodiments. In some embodiments, the motion sensing unit is located on the WCD so that it is positioned in a known orientation on the patient's back when the WCD is worn by the patient.

Walking detection module 236A is configured to process the output signals from motion sensing unit 281A to determine whether the patient is walking or running, and the patient's orientation in some embodiments. When the external defibrillator 201A is worn by a patient, motion sensor signals can indicate actual patient motion such as from walking (sometime referred to herein as subject motion), as well as motion such as from riding in a vehicle (sometimes referred to herein as ambient motion), or from both subject and ambient motion simultaneously. These types of motion can also cause artifact in the ECG signals that may lead to false positive detections of life-threatening arrhythmias. The motion sensing signals from motion sensing unit 281A can be analyzed by the walking detector module 236A of processor 230 to distinguish subject motion (e.g. walking) from other types of motion (e.g., ambient motion) that would not rule out a shock recommendation. As previously described, subject motion would rule out a shock recommendation by a WCD. In some embodiments, the motion sensing unit 281A provides output signals from which walking detector module 236A can determine the patient's orientation. Further some embodiments also use the determined orientation to distinguish between subject and ambient motion. For example, a patient determined to have a "lying down" orientation would not likely be walking or running, so this orientation information can be used to distinguish between subject and ambient motion. Detection of walking is advantageous because: (1) in general patients who are walking are not in cardiac arrest and do not need to be shocked; (2) ECG artifacts often occur when a person is walking, possibly obscuring the ECG; (3) walking has a distinct accelerometer signature that is easily identified; and (4) walking is an activity that almost every patient engages in so it is advantageous for a WCD to be able to recognize walking and account for it in its rhythm analysis (e.g., detecting walking allows a WCD to correctly confirm that the patient does not need to be shocked even if the ECG signal is obscured by artifact).

Because walking and running can cause motion artifact in the ECG signal, in some embodiments, walking detector module 236A is also configured to cause processor 230 to issue an alert to the patient to address potential motion artifact under certain circumstances (e.g., the WCD detects an elevated HR or QRS width that may be due to or obscured by motion artifact from the patient walking or running). For example, the alert can notify the patient to wet the ECG electrodes, or to stop walking or running so that the WCD can analyze an ECG with reduced motion artifact.

Figure 3:
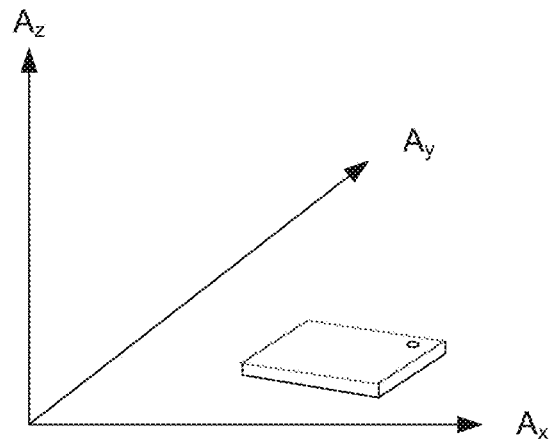
FIG. 3 is an example three-axis acceleration system for an accelerometer and the associated position of the accelerometer, according to embodiments of this disclosure.

Referring to FIG. 3, a motion sensor, such as the motion sensing unit 281A shown in FIG. 2A, in some embodiments is implemented using an accelerometer. Such an accelerometer may be used to determine a patient's position and/or movement. The motion sensor of FIG. 3 may be included in one of the monitoring devices 180 (FIG. 1) and/or 281 (FIG. 2) or may be a separate component in the WCD system or may be another wired or wirelessly connected sensor or monitoring unit (e.g., fitness monitors incorporated in mobile communication device, wrist bands, or other apparel such as socks or shoes). In some embodiments, the motion sensor includes an accelerometer that provides sensed acceleration signals in 3 orthogonal axes, as will be described below in conjunction with FIGS. 3-6. In various embodiments, walking detection module 236A (FIG. 2A) can analyze one axis signal, 2 axes signals, or all 3 axes signals to determine the acceleration component in the vertical or "up-down" direction (i.e., up and down relative to the center of the earth or in the same direction as earth's gravity), depending on the orientation of the motion sensor. Walking detection module 236A (FIG. 2A) can run continuously in real-time mode and optionally run simultaneously with a segment-based analysis for a more advanced analysis. and if included, a posture change detector In the below examples (e.g., the embodiments used for FIGS. 3-7), the motion sensing unit 281A (FIG. 2A) is positioned and/or oriented so that the Y axis represents the "up-down" direction when a patient stands or sits straight up or is walking/running. After review of the teachings of the present disclosure, those skilled in the art of WCDs will be able to implement other embodiments in which the up-down direction is aligned with the X or Z axes, and still other embodiments in which the up-down direction is not aligned with one of the orthogonal axes using trigonometric methods to find the acceleration measurement in the up-down direction. Walking detection module (FIG. 2A) can be used to determine that the patient is walking or running based on the footstep intervals, the amplitude of accelerometer signal, and/or the frequency content of the signal received from motion sensor unit 281A, as described in more detail below.

FIG. 3 illustrates a three-axis acceleration measurement system for an accelerometer and the associated position of the accelerometer. As an example, the Y axis represents the up-down activity when a patient stands or sits straight up. However, as will be understood in view of the present disclosure by one skilled in the art, the accelerometer may be oriented such that either one of the other axes may represent the up-down activity.

Figure 4:
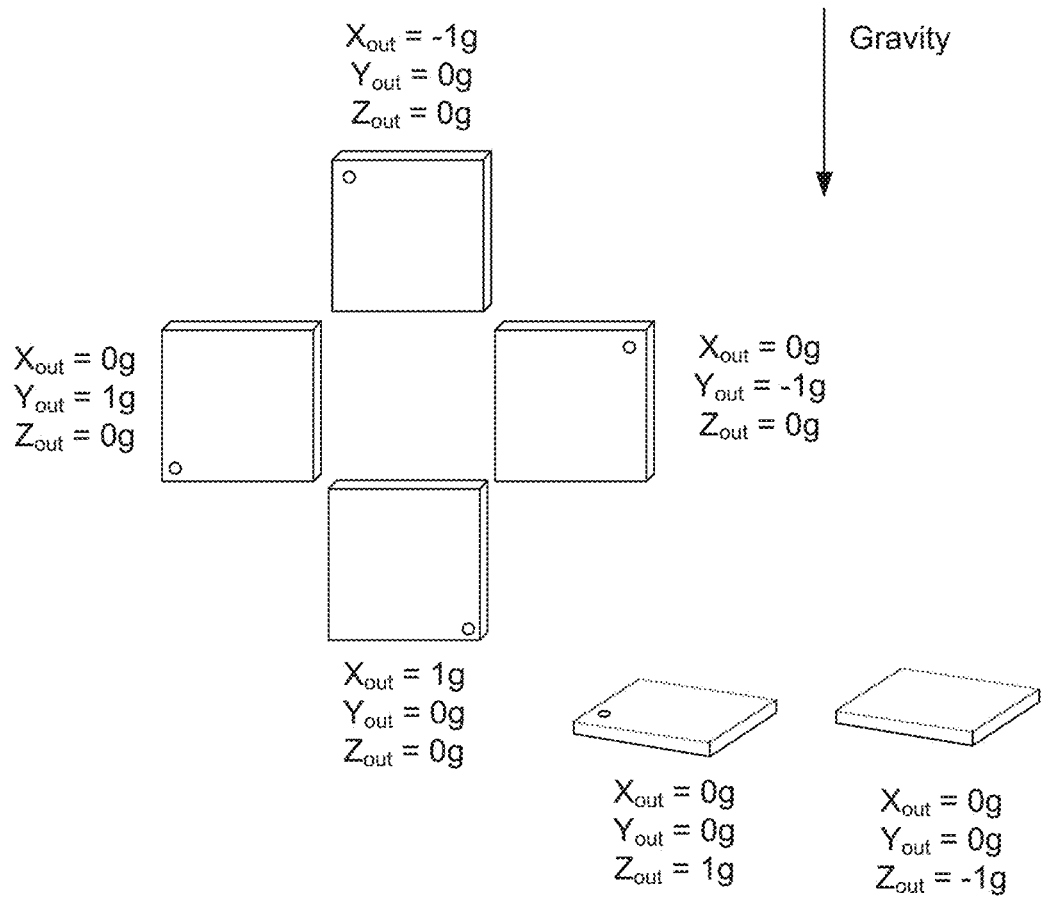
FIG. 4 is an illustration of the various orientations and outputs from the accelerometer in such orientations, according to embodiments of this disclosure.

FIG. 4 illustrates the various orientation of the accelerometer and the readings provided based on the orientation shown in FIG. 3. For example, if the patient is standing or sitting upright, the $Y_{out}$ from the accelerometer will be −1 g, while $X_{out}$ and the $Z_{out}$ will be 0. When a patient is in a supine position, $Z_{out}$ is −1 g, while $X_{out}$ and $Y_{out}$ are zero. When the patient is lying on their right side, $X_{out}$ is −1 g, while $Y_{out}$ and $Z_{out}$ are zero.

A patient's actual hemodynamic status typically is not available to the WCD system via standard physiological measures, such as blood pressure, arterial pressure, temporal monitoring, etc. and the decision of rapid or slow therapy delivery via devices has historically been made based on the rate and/or morphology of the ECG signals. However, a surrogate for hemodynamic status may be patient posture. The WCD system disclosed herein then may shock a patient even if the heart rate is in the monitor zone or VT zone when the processor 230 detects a patient has suddenly fallen and hemodynamically instable.

Figure 5:
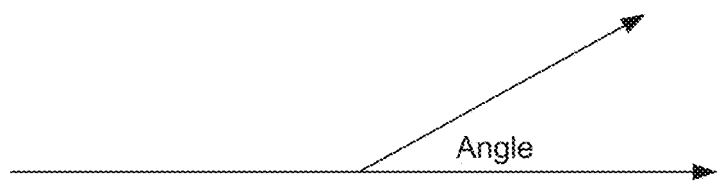
FIG. 5 is an example angle of a patient lying down from the accelerometer, according to embodiments of this disclosure.
Figure 6:
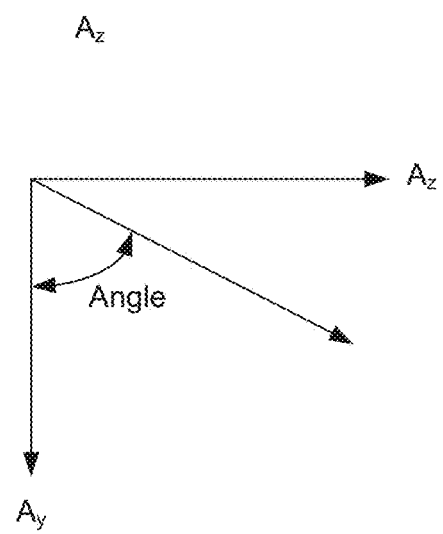
FIG. 6 is an example angle of a patient in an upright position from the accelerometer, according to embodiments of this disclosure.

A patient's posture is determined to be in a lying position when an angle is thirty degrees or less from the $A_Z$ axis, as shown in FIG. 5. For example, the patient is lying down when Y is between −0.5 g and 0.5 g. FIG. 6 illustrates an angle for measuring the upright position of the patient. For example, the angle would be zero when the patient is standing upright and would be ninety degrees when the patient is in the supine position. The WCD system, however, may consider any angle below thirty degrees to be an upright position in some embodiments.

As mentioned above, the patient's posture and/or movement determined by the motion sensor may be used to detect a sudden posture change and subsequent motion, or lack thereof, after the posture change of the patient.

Figure 7:
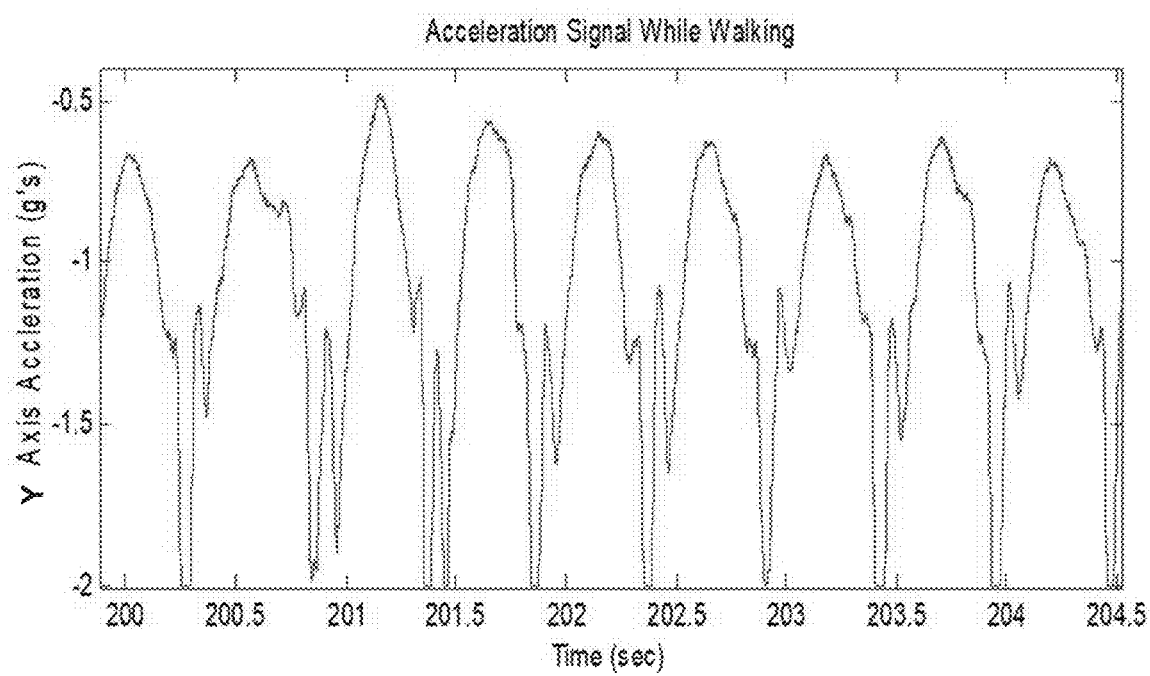
FIG. 7 is a chart illustrating an example of the measured acceleration along the Y-axis while a patient is walking, according to embodiments of this disclosure.

FIG. 7 is a chart illustrating an example of the measured acceleration along the Y-axis while a patient is walking, according to embodiments of this disclosure. The patient's acceleration along the Y-axis (up-down direction) in this example has a dynamic range of about 1.5 G magnitude and generally has a magnitude above 0.5 G. In some embodiments and depending on the motion sensor configuration and orientation, this range can be based on the typical acceleration output signal for standing still (e.g. −1 G) and walking (e.g., lower than −1.5 G). In embodiments, a parameter (referred to herein as a "Bouncy" parameter) is determined from Y-axis acceleration measurements. In some embodiments, the Bouncy value is a measurement of the AC component of the Y-axis accelerometer signal. In embodiments, the AC component measurement can include a peak-peak value measurement, an RMS measurement of the signal after the mean value has been removed, or an FFT of the acceleration signal. In standard step counter devices, accurate detection of steps can be defeated, for example, by shaking the step-counter device. However, embodiments using the Bouncy parameter are more sophisticated and can accurately distinguish real steps/walking from "shaking" and from ambient motion.

Embodiments for determining the Bouncy value are described in more detail below in conjunction with FIG. 9, but before describing these embodiments, the use of the Bouncy parameter (to detect walking or running) in a rhythm analysis algorithm is described in conjunction with FIG. 8.

Figure 8:
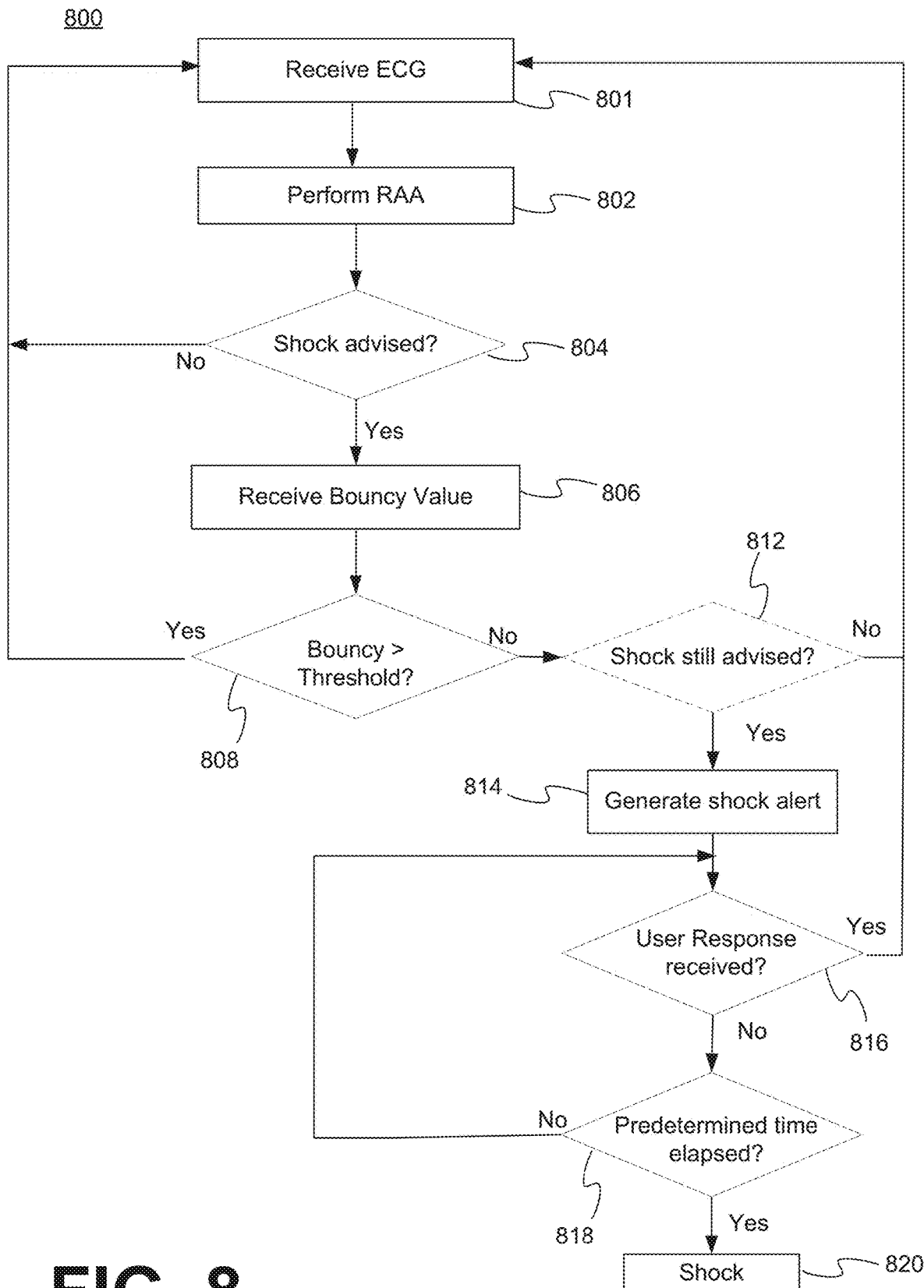
FIG. 8 is an example flow chart illustrating an example process for determining whether to provide a shock to a patient, according to embodiments of this disclosure.

FIG. 8 is an example flow chart illustrating an example process 800 for determining whether to provide a shock to a patient using a Bouncy parameter, according to embodiments of this disclosure. Embodiments of process 800 may be executed by processor 230 (FIG. 2A) and motion sensing unit 281A (FIG. 2A) in external defibrillator 201A (FIG. 2A). For example, detection module 232, advice module 234 and walking detection module 236A of processor 230 in some embodiments implement a rhythm analysis algorithm (RAA) to make a "shock/no shock" decision. In embodiments, the RAA includes a QRS detection algorithm. In some embodiments, one or portions of process 800 are implemented using a rules-based system. For example, in some embodiments, rules-based systems are used in the detection of walking or running based on analysis of motion sensor, ECG and step detection information (which in turn can be from rules-based systems).

Some embodiments of process 800 are specifically designed to detect walking, running and/or posture changes and, in response to detecting such walking, running, and/or certain posture changes, to inhibit a shockable rhythm indication by the RAA. If any activity above a threshold inhibits or delays a shockable rhythm indication, then there might be a possibility that a shockable rhythm which already started before the activity will not be treated properly. So, in some embodiments, process 800 is performed before any initial VT/VF detection. Once VT/VF is confirmed, walking detection process 800 can be disabled to avoid false negative detection that can improperly inhibit treatment.

In embodiments, a patient profile (obtained by clinicians when prescribing and fitting the WCD to the patient) and the walking detection functionality of external defibrillator 201A can be used together by processor 230 to estimate the HR (heart rate) based on the activity. In some embodiments, the activity level and HR range of the patient can be included in the patient profile for example, to be used in calibrating thresholds used in various embodiments of process 800.

In process 800, an operation 801 is performed to receive a patient's ECG signal. Referring to FIGS. 2, 2A and 8, in some embodiments, operation 801 is performed by processor 230 via measurement circuit 220, ECG port 219 and ECG electrodes 209.

In an operation 802, a Rhythm Analysis Algorithm (RAA) is performed. In some embodiments, operation 802 is performed by processor 230 (FIG. 2A). The RAA can be implemented as disclosed in U.S. Pat. No. 9,592,403, which is incorporated herein by reference in its entirety. In some embodiments, the RAA is segment-based, using successive fixed length segments of ECG signal stored in a buffer. Each fixed length segment is about 4.8 seconds in some embodiments, but in other embodiments the length can range from 2 to 20 seconds. In embodiments, the RAA uses the most recent 13 segments in making a shock-no shock decision, but in other embodiments the number of segments can range from 3 to 50. In some embodiments, the RAA uses information related to the patient's detected heart rate (HR) and the width of the QRS complexes. This information is determined from the patient's ECG signal in some embodiments. In some embodiments, the patient's HR is determined as described in U.S. application Ser. No. 16/140,324 entitled "HEART RATE CALCULATOR WITH REDUCED OVERCOUNTING" filed Sep. 24, 2018, 2018, which is incorporated herein by reference in its entirety.

In an operation 804, the shock/no shock decision from the RAA is analyzed. In some embodiments, this operation is performed by processor 230 (FIGS. 2, 2A). If the RAA indicates a shock is not advised, process 800 loops back to operation 801 to continue to monitor the patient's ECG signals. However, if the RAA indicates that a shock is advised, process 800 proceeds to an operation 806.

In operation 806, a Bouncy value is received for the time-period corresponding to the ECG signal received in operation 801. Embodiments of how the Bouncy value is determined are described below in conjunction with FIG. 9. In some embodiments, the Bouncy value is received from motion sensing unit 281A (FIG. 2A), for example in embodiments in which motion sensing unit 281A is configured with a processor and algorithm for determining the Bouncy value from motion sensor data. In other embodiments the Bouncy value is determined by processor 230 using motion sensing data from motion sensing unit 281A. In still other embodiments, the Bouncy value is received from walking detector module 236A (FIG. 2A) after it determines the Bouncy value from the output signals from motion sensing unit 281A. In other embodiments, the Bouncy value may be received from other components or units, for example, components or units with motion sensors such as step counters, fitness trackers, smartphones, etc. that are configured with an algorithm for determining the Bouncy value from motion sensor data.

In an operation 808, the Bouncy value is analyzed. In some embodiments, the Bouncy value is analyzed by processor 230, for example, by walking detector module 236A of processor 230. In some embodiments, if the Bouncy value is determined to be greater than a predetermined or preset threshold (i.e., indicating that walking/running is detected), process 800 returns to operation 801. In some embodiments, the threshold is 0.5, but in other embodiments the threshold can range from 0.3 to 0.8. As previously described, a walking/running patient is not in need of a shock, so process 800 returns to monitoring the patient's ECG without generating a shock alert. This path avoids unnecessarily interrupting, distracting, stressing etc. the patient with a false alarm while the patient is walking or running. However, if the Bouncy value is determined to be less than the threshold, process 800 proceeds to an operation 812.

Operation 812 is shown in dashed lines in FIG. 8, indicating that it is optional. In some embodiments in which the Bouncy value is calculated and analyzed (i.e., operations 806 and 808) independently of the operations 801, 802 and 804 related to rhythm analysis, operation 812 may be performed to ensure that a shock is still advised by the RAA. In other embodiments, additional analysis may be performed (in addition to or instead of the RAA recheck) to increase the accuracy of a walk detection. Different embodiments for operation 812 are described below in conjunction with FIGS. 12 and 13-19.

In some embodiments, operation 812 when performed is performed by processor 230. If it is determined that a shock is no longer advised, process 800 returns to operation 801. Stated another way, operations 808 (and 812 if performed) determine whether the patient is walking or running. If the patient is walking or running, as previously described, the patient is not shocked. In addition, in some embodiments in which the RAA uses a QRS detector, when it is detected that the patient is walking/running, the RAA QRS detector can be modified to be less sensitive to the motion artifact. This feature can be advantageous because reducing the sensitivity can reduce false QRS detections caused by motion artifact.

However, if it is determined that a shock is still advised, process 800 proceeds to an operation 814. In embodiments that are not configured with operation 812 (for example in embodiments in which the RAA and the walking detection analysis are performed concurrently), operation 808 proceeds directly to operation 814. In some embodiments in which the RAA is a segment-based analysis, the walk detection is part of the segment analysis. For example, in some embodiments, the RAA is segment-based and uses a state machine to determine the system behavior, such as alarms and therapy delivery. In such embodiments the walking detection is processed as a part of the segment analysis and operation 812 can be omitted.

In operation 814, a shock alert is generated. In some embodiments, this operation is performed by processor 230 and user interface 280 (FIG. 2). For example, processor 230 can instruct user interface 280 to generate a shock alert that can be in the form of an audio, visual, vibration, haptic, or electrical indication (or any combination of these indications) to warn the patient and bystanders of the impending shock.

In an operation 816, process 800 determines whether a user response to the shock alert was received to divert therapy. In some embodiments, processor 230 is configured to check whether such a response has been received from a user via user interface 280 (FIG. 2). In some embodiments, user interface 280 includes one or more buttons that the patient activates to divert the shock. In other embodiments, the user interface can be configured to receive other types of responses to divert therapy such as, for example, voice recognized responses, biometric responses, tapping, gestures, etc. including combinations of these responses. If a response is received, in some embodiments process 800 aborts or disregards the shock determination and returns to operation 801 to recommence monitoring the patient's ECG. If a response in not received, process 800 proceeds to an operation 818.

In operation 818, process 800 determines whether a preset, preselected or predetermined time (hereinafter "predetermined time") has elapsed since the shock alert was generated in operation 814. In some embodiments, operation 818 is performed by processor 230 and the predetermined time may depend on one or more factors (e.g., whether the RAA determined the rhythm was VF or VT, whether a previous shock was administered, configuration settings entered by a clinician, etc.). If it is determined that the predetermined time has not elapsed, process 800 returns to operation 816 to check whether a response has been received from the user to divert therapy. However, if it is determined that the predetermined time has elapsed, process 800 proceeds to an operation 820 in which external defibrillator 201A is controlled to deliver a shock to the patient. In some embodiments, processor 230 controls the charging of energy storage module 250 and the operation of discharge circuit 255 to deliver a shock via defibrillation port 210. In some embodiments, in addition to, or instead of, shocking the patient, processor 230 may initiate a communication with a remote center, such as a hospital, emergency response center (e.g., calling "911"), or any other remote center, to get necessary help. This may be especially beneficial if the detected heart rate is in the monitor zone or the VT zone, and/or if the WCD has administered the maximum number of shocks that it has been configured to deliver. Although not shown in FIG. 8, after the shock is administered, in embodiments the WCD returns to operation 801 to resume monitoring the patient's ECG to determine if the shock was successful and if not, provide an additional shock.

Figure 9:
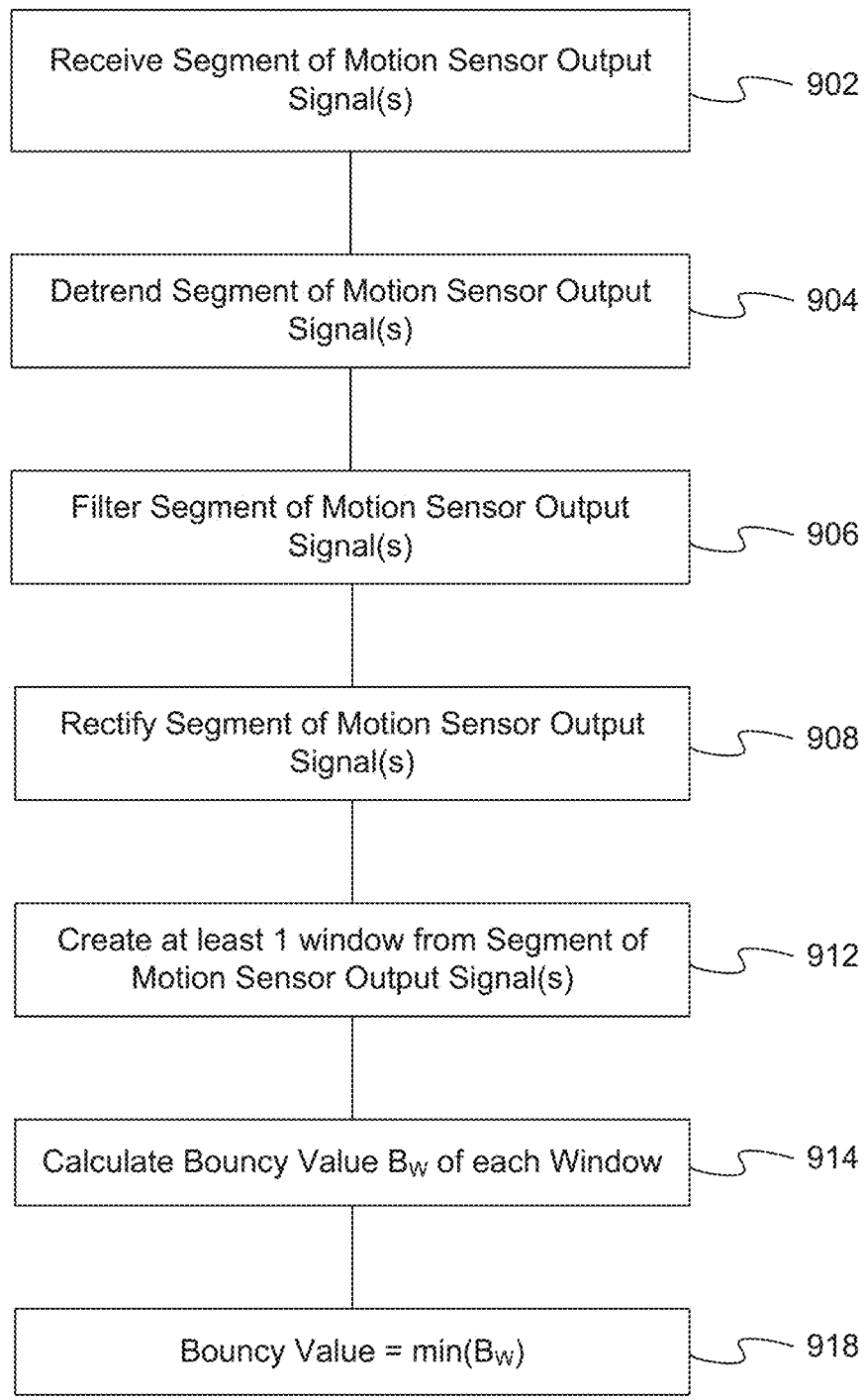
FIG. 9 is an example flow chart illustrating an example process for determining a Bouncy Value, according to embodiments of this disclosure.

FIG. 9 is an example flow chart illustrating an example process 900 for determining a Bouncy Value, according to embodiments of this disclosure. As previously described, embodiments of process 900 may be implemented by: motion sensing unit 281A (FIG. 2A); processor 230 (FIG. 2A) using output signals from motion sensing unit 281A (FIG. 2A) with or without using walking detector module 236A; or a combination thereof performing operations 902, 904, 906, 908, 912, 914 and 918 as described below.

In operation 902, a segment of motion sensor output signal (or signals) is received. In some embodiments, the motion sensor output signals are 3-axis accelerometer signals. In some embodiments, the output signals indicate the patient's acceleration in the up-down axis (i.e., the Y-axis in the embodiment of FIG. 7) and the segment length is about 4.8 seconds. In other embodiments, the segment length can range from 2 to 30 seconds.

In operation 904, a detrend process is performed on the received segment to account for "drift" in the motion sensor output. In some embodiments, processor 230 performs this operation using a detrend algorithm that subtracts the mean value from the signal, calculates and cancels out the slope of the signal. In alternative embodiments, motion sensing unit 281A performs the detrend algorithm. In some embodiments, operation 904 can be omitted.

In operation 906, the received segment is filtered. In some embodiments, processor 230 (or motion sensing unit 281A) digitally filters the segment. For example, in some embodiments the digital filter is a low pass filter at 3 Hz, or a high pass filter at 1 Hz. In one embodiment, both a low pass filter at 3 Hz and a high pass filter at 1 Hz for a band pass filter is implemented. In some embodiments, this filtering can make the detrending of operation 904 unnecessary. In other embodiments, operation 906 can be performed using one or more analog filters coupled to receive the output signals from the motions sensing unit 281A to low pass, high pass, or band pass filter motion sensor output signals.

In operation 908, the received segment is rectified. In some embodiments, processor 230 (or motion sensing unit 281A) rectifies the received segment. For example, as describe above the received segment in some embodiments is the accelerometer signal representing the acceleration in the up-down or Y-direction, and the rectified segment represents the magnitude of the acceleration of the received segment at points in the segment duration.

In operation 912, at least one window is created from one or more segments of the motion sensor output signals. In some embodiments, two 2.4 second windows are created from one 4.8 section segment. In other embodiments the number of windows can range from 1 to 5 windows. In still other embodiments, the windows can overlap, or a window can be slid over the segment in one sample (for example) increments to generate a large set of windowed values.

In operation 914, for each window created in operation 912, a Bouncy value ($B_W$) is calculated from the portion of the rectified segment in that window. In some embodiments, the $B_W$ is determined as the fraction of the rectified signal that exceeds a Bouncy threshold (e.g. 0.05 G). In other embodiments the Bouncy threshold can range from 0.3 to 0.8. Each $B_W$ will be between 0 and 1, and a higher value in effect represents a higher activity level.

In operation 918, the Bouncy value for the segment is calculated as the minimum $B_W$ of the one or more windows of that segment. In other embodiments, different algorithms may be used to determine the Bouncy value from the $B_W$ of each window of the segment (e.g., a mean, median, maximum, etc. In still other embodiments, instead of determining a Bouncy value, a ratio of the number of segments above and below a threshold is determined and compared to a ratio that indicates walking.

As described above, each BW will be between 0 and 1, so the Bouncy value will also necessarily be between 0 and 1. Referring back to operation 808 (FIG. 8), if the Bouncy value is greater than the Bouncy threshold, the activity is considered to be motion that is initiated or performed by the patient under the patient's volition (also referred to in this context as "patient-specific motion" or "subject motion"), such as walking, running, etc. According to embodiments, such patient-specific motion may preclude a decision to shock by the WCD. Also, as described above, in certain scenarios the patient may undergo motions that are not patient-specific such as, for example, being in a car, bus, motorcycle, airplane, elevator, amusement park ride, earthquakes, or other apparatus or phenomena that can move the patient (also referred to herein as "ambient motion"). One such scenario is described below in conjunction with FIG. 10.

Figure 10:
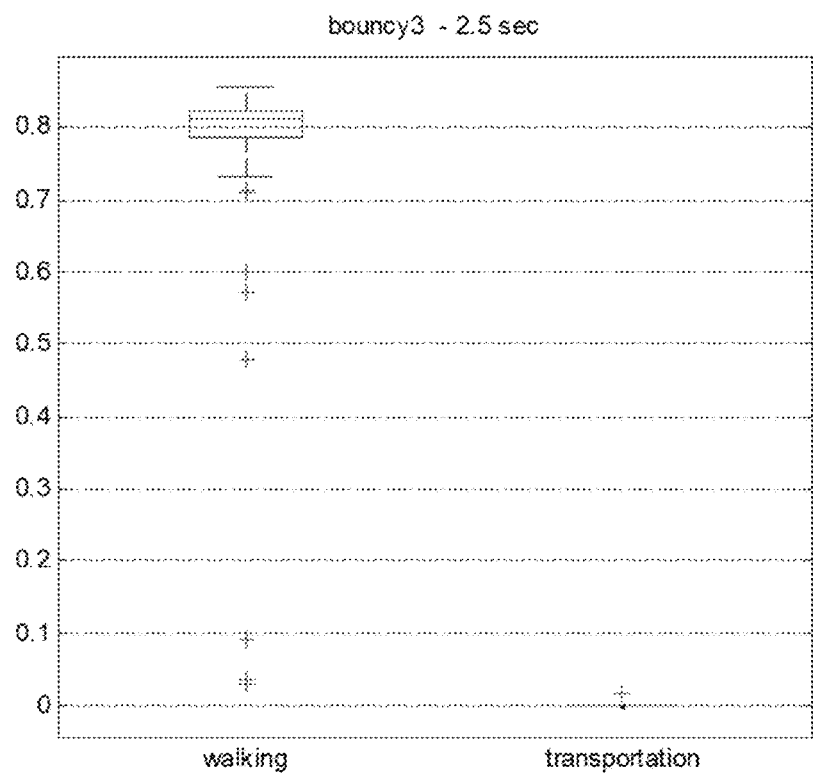
FIG. 10 is a chart illustrating an example of Bouncy Values determined for a walking patient and for a patient being transported in a vehicle, according to embodiments of this disclosure.

FIG. 10 is a chart illustrating an example of Bouncy values determined for a walking patient and for a patient being transported in a vehicle, according to embodiments of this disclosure. As shown in the chart of FIG. 10, walking generates Bouncy values ranging from about 0.8 to about 0.03, while riding in a vehicle generates Bouncy values within a narrow range about 0.01. Based on an analysis of Bouncy values in various scenarios, the inventors of the present disclosure have developed algorithms for defining the Bouncy values, and algorithms using the Bouncy values to distinguish between motion due to walking and motion due to transport in a vehicle. For example, in some embodiments, an algorithm uses the analyses that the range of Bouncy values for people walking is relatively large and well above the range of Bouncy values for vehicle transport and thus, can be used to accurately detect waking and to distinguish between walking and transport in a vehicle.

Figure 11:
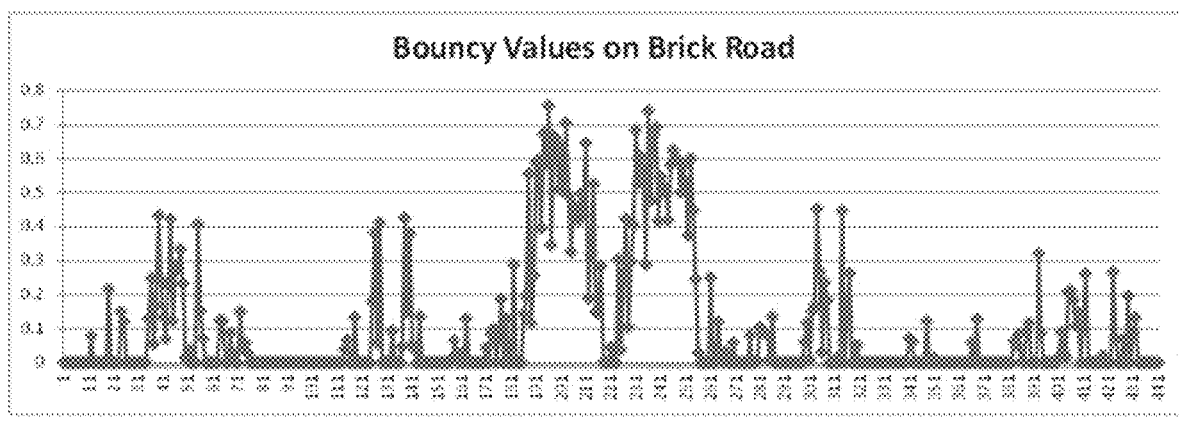
FIG. 11 is a chart illustrating an example of Bouncy Values as a function of time determined for a patient being transported in a vehicle over a brick road, according to embodiments of this disclosure.

FIG. 11 is a chart illustrating an example of Bouncy Values as a function of time determined for a patient being transported in a vehicle over a brick road, according to embodiments of this disclosure. The chart of FIG. 11 reflects the Bouncy values calculated for two windows for each non-overlapping 5 second segments. As can be seen, the Bouncy values generated while traveling on a brick road can range up to about 0.75, which is similar in value to Bouncy values generated during walking. Some embodiments incorporate one or more additional algorithms to distinguish between patient-specific motion (e.g., walking and running) and various ambient motions. FIG. 12 and FIGS. 13-19 illustrate various embodiments of such additional algorithms.

Figure 12:
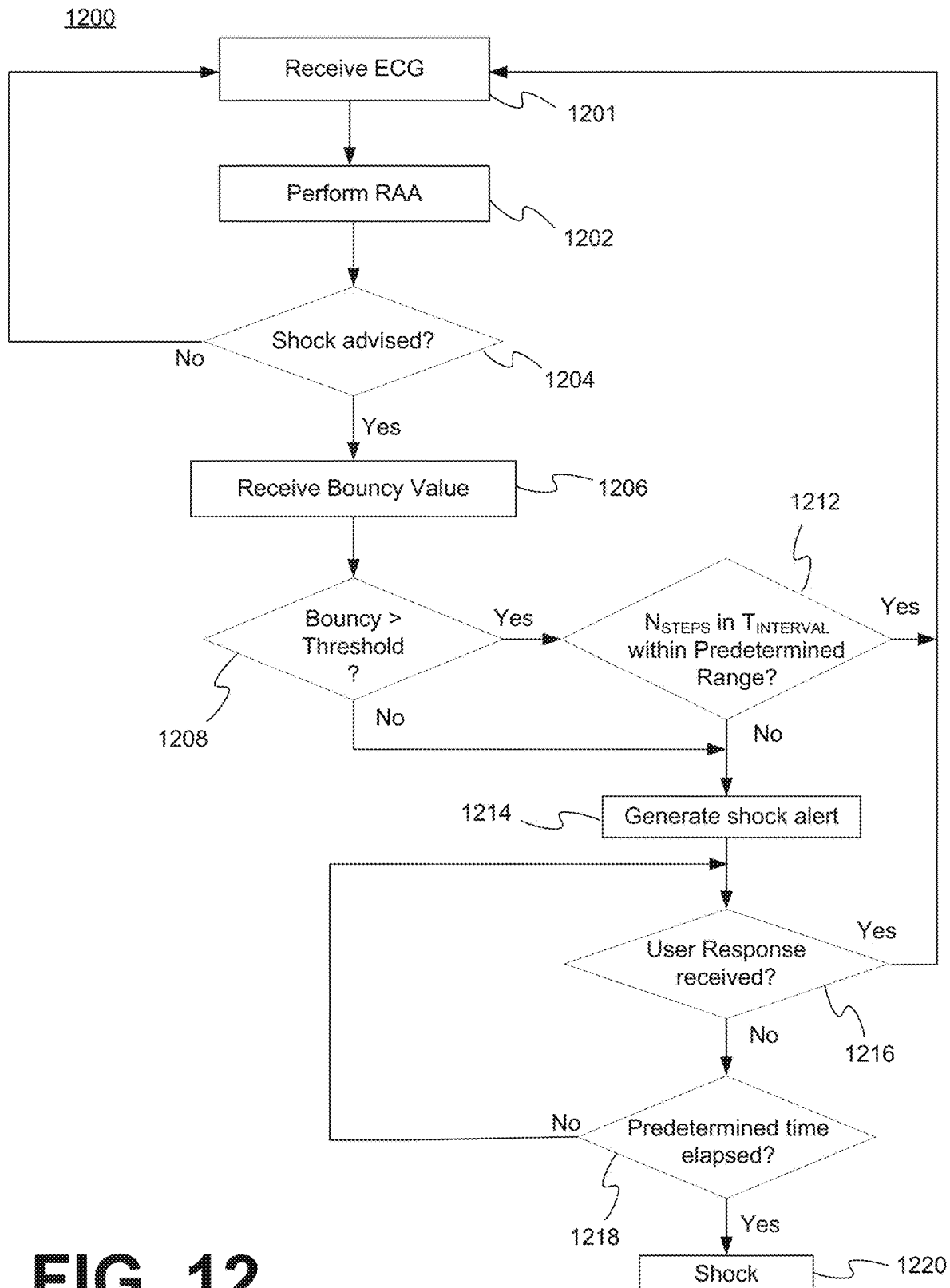
FIG. 12 is an example flow chart illustrating another process for determining whether to provide a shock to a patient, according to embodiments of this disclosure.

FIG. 12 is an example flow chart illustrating other embodiments of a process 1200 for determining whether to provide a shock to a patient. Embodiments of process 1200 are substantially similar to the embodiments of process 800 (FIG. 8), but with operation 812 being replaced with an operation 1212. More particularly, embodiments of operations 1201, 1202, 1204, 1206, 1208, 1214, 1216, 1218, and 1220 in FIG. 12 are substantially similar to operations 801, 802, 804, 806, 808, 814, 816, 818, and 820 previously described in conjunction with FIG. 8.

In operation 1212 (performed in response to a determination that the Bouncy value exceeds a Bouncy Threshold), the number of steps ($N_{STEPS}$) in a preselected time interval (e.g., the duration of a segment in some embodiments) is analyzed to determine if the number of steps within the time interval falls within one or more preselected ranges indicative of walking or running.

Figure 12A:
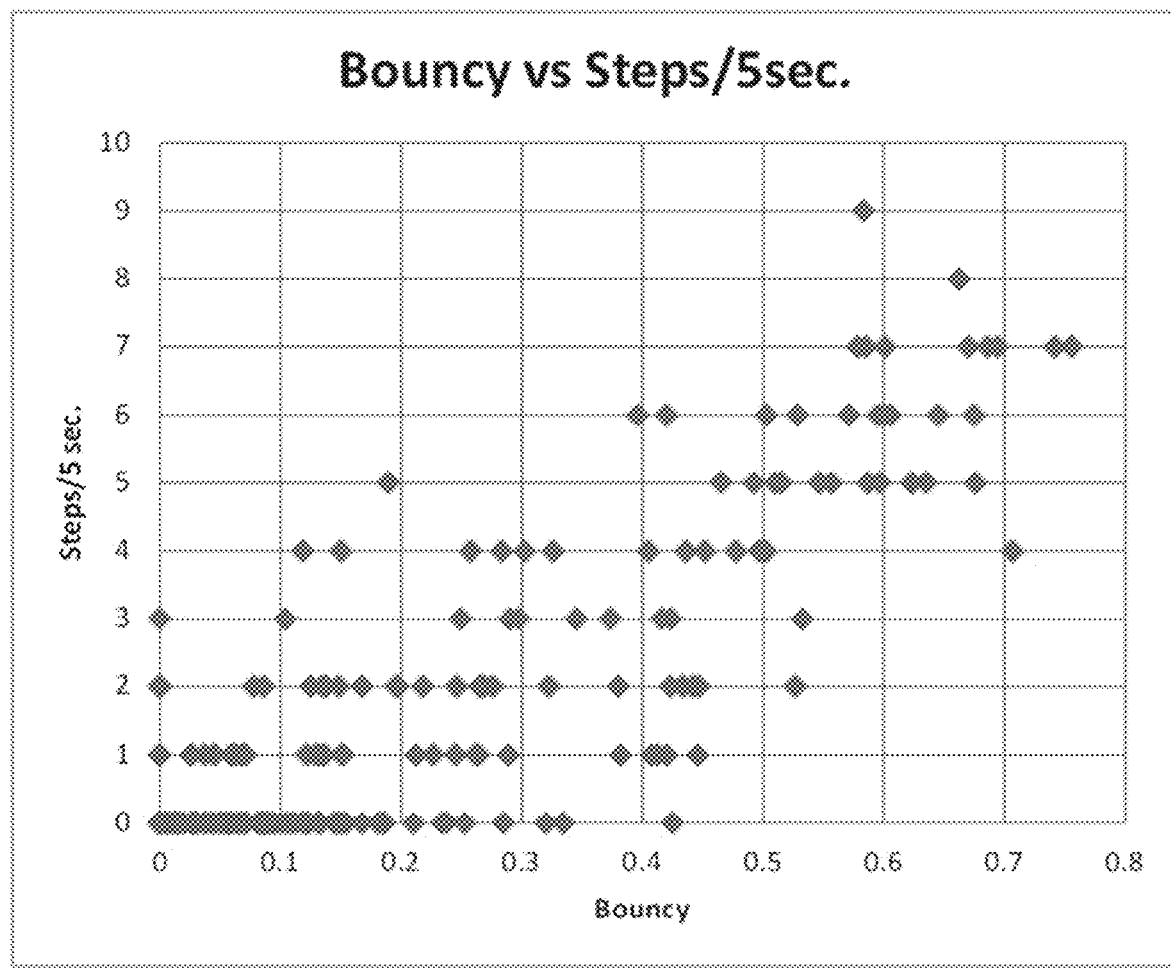
FIGS. 12A and 12B illustrate examples of step interval parameters measured and calculated for a walking patient, according to embodiments of this disclosure.

For example, a test subject wearing motion sensor and processor as described above in conjunction with FIG. 2A was analyzed while being transported over a bumpy road. The number of steps in each of 441 intervals (the intervals in this example are segments of about 5 sec. each) was counted, the output signals of the motion sensor was analyzed, and Bouncy values for each of the 441 intervals was calculated. The data is shown in FIG. 12A.

After careful analyses and processing of motion detector signals for Bouncy values and step counting, the inventors of the present disclosure have determined that: (a) walking and running generate accelerometer waveforms with a morphology and/or pattern that can be used to count steps; (b) walking and running have step intervals ranging between about 300-1000 ms; and (c) certain ambient motions (example transport on brick roads) do not have step intervals within the range of 300-1000 ms. The inventors have used these analyses to develop algorithms for distinguishing walking and running from ambient motion that generates relatively high Bouncy values. In some embodiments of operation 1212, the range of $N_{STEP}$ within the time interval is based on the step intervals of walking and running. For example, in some embodiments the range is set to 5 to 17 steps in a 5 second interval.

Referring again to FIG. 12A, using criteria of a) $N_{STEPS}$>5 steps per 5 second interval for operation 1212 and (b) Bouncy value>0.5 for operation 1208, only 18 of the 441 intervals satisfied the criteria. This represents a false walking detection rate of about 4%. In other embodiments, the criteria can be adjusted (e.g., by raising the $N_{STEPS}$ and/or minimum Bouncy value thresholds, and/or requiring walking detection in several consecutive segments) to further reduce the false detection rate while potentially increasing the false negative rate.

Referring back to FIG. 12, in some embodiments of operation 1212, the steps are counted used using circuitry and algorithms from conventional step counters (e.g., used in fitness trackers, pedometers, etc.). In other embodiments, a real-time step detector algorithm as described below is used. This step detector algorithm is in effect a modified version of a QRS detector used in some monitors and defibrillators (including WCDs). The algorithm is applied to the motion detector signals, and peaks in amplitude are assumed to be a generated by steps. The algorithm is designed to accommodate the variability in the amplitudes of motion sensor signals from different patients when walking.

Figure 12B:
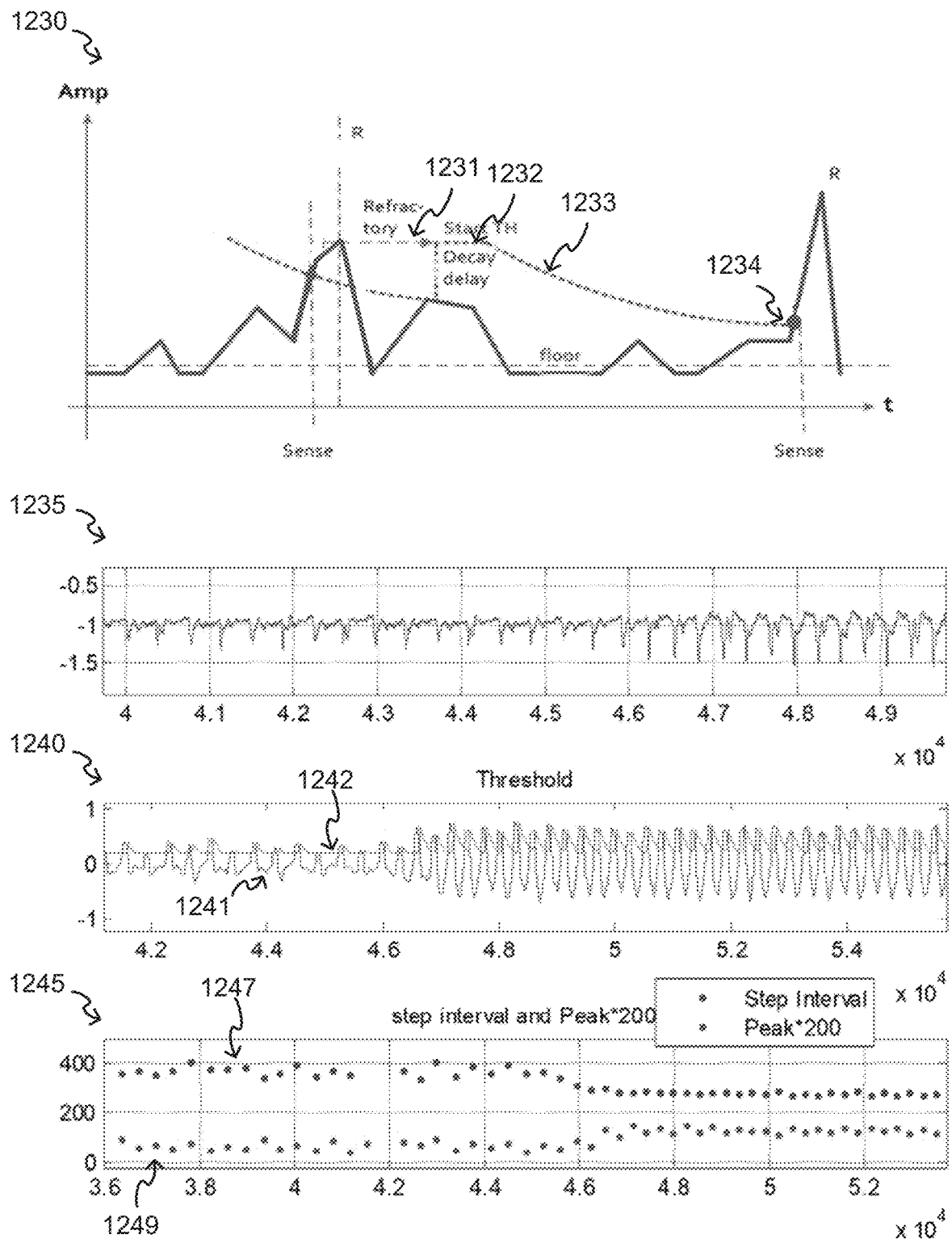

FIG. 12B includes a chart 1230 that illustrates a real-time step detector algorithm according to embodiments. In embodiments, a "Decay" threshold is defined to vary with an exponential delay of a detected peak in the motion sensor signals. When the amplitude rises above the Decay threshold, the algorithm outputs that a step is detected. However, in some embodiments a refractory period is defined based on the minimum step interval for walking so that after a step is detected, the next step cannot be detected until after the refractory period expires.

In some embodiments, the Decay threshold is bounded within certain limits such as a minimum (shown as the "floor" in FIG. 12B), and/or a value that is based on previous peak amplitude. For example, in some embodiments the minimum Decay threshold is ⅓ of the previous peak amplitude with a floor of 0.2 G. In some embodiments, the decay starts after the refractory period, while in other embodiments the decay starts after the refractory period plus an additional decay delay (DD). According to some embodiments, the Decay threshold (TH) for the real-time step detector algorithm can be determined according to equations (1) and (2):

$$TH(t) = TH_{START} \text{ for } t < (\text{refractory period} + DD); \text{otherwise} \quad (1)$$

$$TH(t) = \text{Max}[TH_{START}(e^{-t/0.35}), (TH_{START})/SMR, \text{Floor}] \quad (2)$$

where the variable "t" is the time since the end of the refractory period (at which t=0), SMR is a sense margin ratio, DD is the decay delay (which can be zero). In the example described above in the previous paragraph, SMR=3 and Floor=0.2 G.

In the example illustrated by chart 1230, the changing value of TH(t) prior to the second "sense" of a patient's step is presented by portions 1231-1233. The refractory period is represented by portion 1231, and the start of the DD (represented by portion 1232) begins at the end of the refractory period. The start of the exponential decay of the threshold TH (represented by portion 1233) begins at the end of the DD. The second "sense" occurs at the time aligned with a point 1234, when the acceleration in the Y-direction is equal to the value of TH(t).

FIG. 12B also includes charts 1235, 1240 and 1245, which illustrate examples of step interval parameters measured and calculated for a walking patient, according to embodiments of a real-time step detector algorithm. The parameters are described further below in conjunction with FIG. 12C.

Figure 12C:
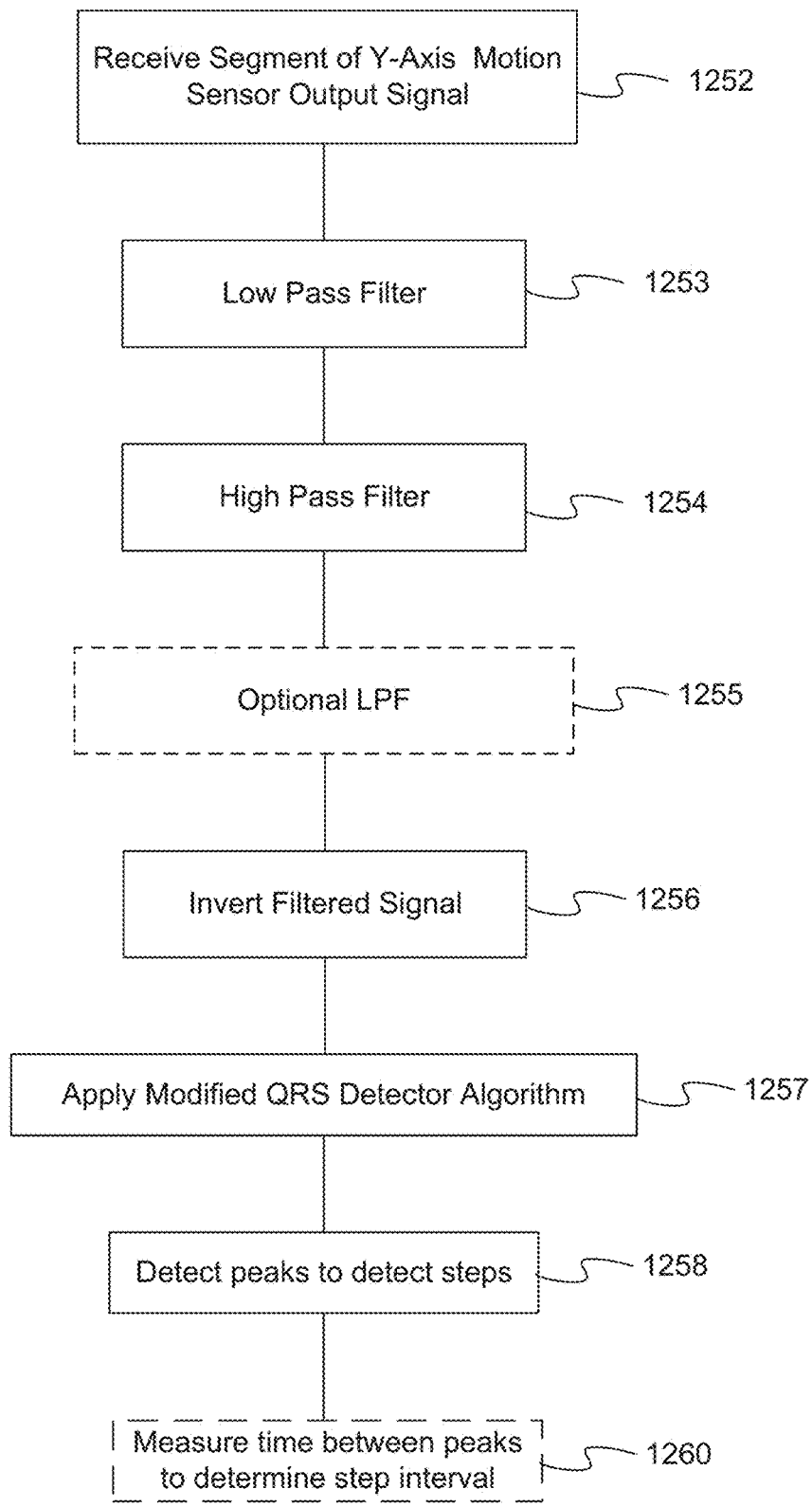
FIG. 12C is an example flow chart illustrating a process for determining step interval for a walking patient, according to embodiments of this disclosure.

FIG. 12C is an example flow chart illustrating an example process 1250 for determining step interval for a walking patient, according to embodiments of this disclosure. Embodiments of process 1250 may be executed by processor 230 (FIG. 2A) and motion sensing unit 281A (FIG. 2A) in external defibrillator 201A (FIG. 2A). For example, detection module 232, advice module 234 and walking detection module 236A of processor 230 in some embodiments implement a real-time step detector algorithm.

In an operation 1252, a segment of a motion sensor signal for the up-down motion (i.e., Y-axis in this example) is received. Chart 1235 (FIG. 12B) shows an example of the received motion sensor signal.

In operations 1253 and 1254, the received segment is low pass filtered and high pass filtered, respectively. In embodiments, the filtering is configured to pass frequencies between 12 Hz and 1 Hz, however in other embodiments the passband can range from any frequency>12 Hz to about 0.1 Hz.

In an operation 1255, the filter segment from operations 1253 and 1254 is filtered again with another filter. In some embodiments, an average of the current and a preselected number of previous samples is calculated and multiplied by a gain. For example, in some embodiments: the acceleration signal is sampled at 500 Hz; the preselected number of previous samples is 99; a mean is calculated of the 100 samples (the current sample and 99 previous samples); and the mean is multiplied by a gain of 5. This in effect implements a low pass FIR filter. In other embodiments, the number of previous samples can range from 100 to 200, and the gain can range from 5 to 10. In some embodiments, operation 1255 is omitted.

In an operation 1256, the output from operation 1255 (or operations 1253 and 1254 if operation 1255 is omitted) is then inverted. This operation accounts for the typical large negative accelerations resulting from the sudden stopping of the patient's feet when striking the ground while walking. The resulting waveform can be more easily processed by the previously described real time step detector algorithm. Chart 1240 (FIG. 12B) shows an example of the filtered signal 1241 as a function of time (ms). In other embodiments operation 1256 is implemented as a rectification of the received filtered signal.

In an operation 1257, the filtered signal is processed using the previously described real-time step detector algorithm to determine the peak or "step detection" thresholds (e.g., TH(t)). Chart 1242 (FIG. 12B) shows an example of TH(t) calculated according to equations (1) and (2) above.

In an operation 1258, the filtered output signal is also processed using the thresholds calculated in operation 1257 to detect peaks. For example, in some embodiments when the filtered signal at time t is equal to or exceeds the threshold, a peak is deemed detected by process 1250. Each detection of a peak corresponds to detecting a patient's step while walking or running. In this way, steps are detected in real-time (i.e., with an insignificant delay from when the step occurred). Chart 1249 (FIG. 12B) shows an example of peaks detected using the threshold TH(t) of operation 1257

In an operation 1260, the time between steps is measured to determine the step interval. Chart 1247 (FIG. 12B) show an example of step intervals corresponding to the steps detected operation 1258. In some embodiments, operation 1260 is performed by counting the number of steps detected in a segment of known duration (e.g., about 5 seconds, and in some embodiments it is 4.8 seconds) to determine an average step interval for that segment, rather than measuring the time between steps.

Figure 13:
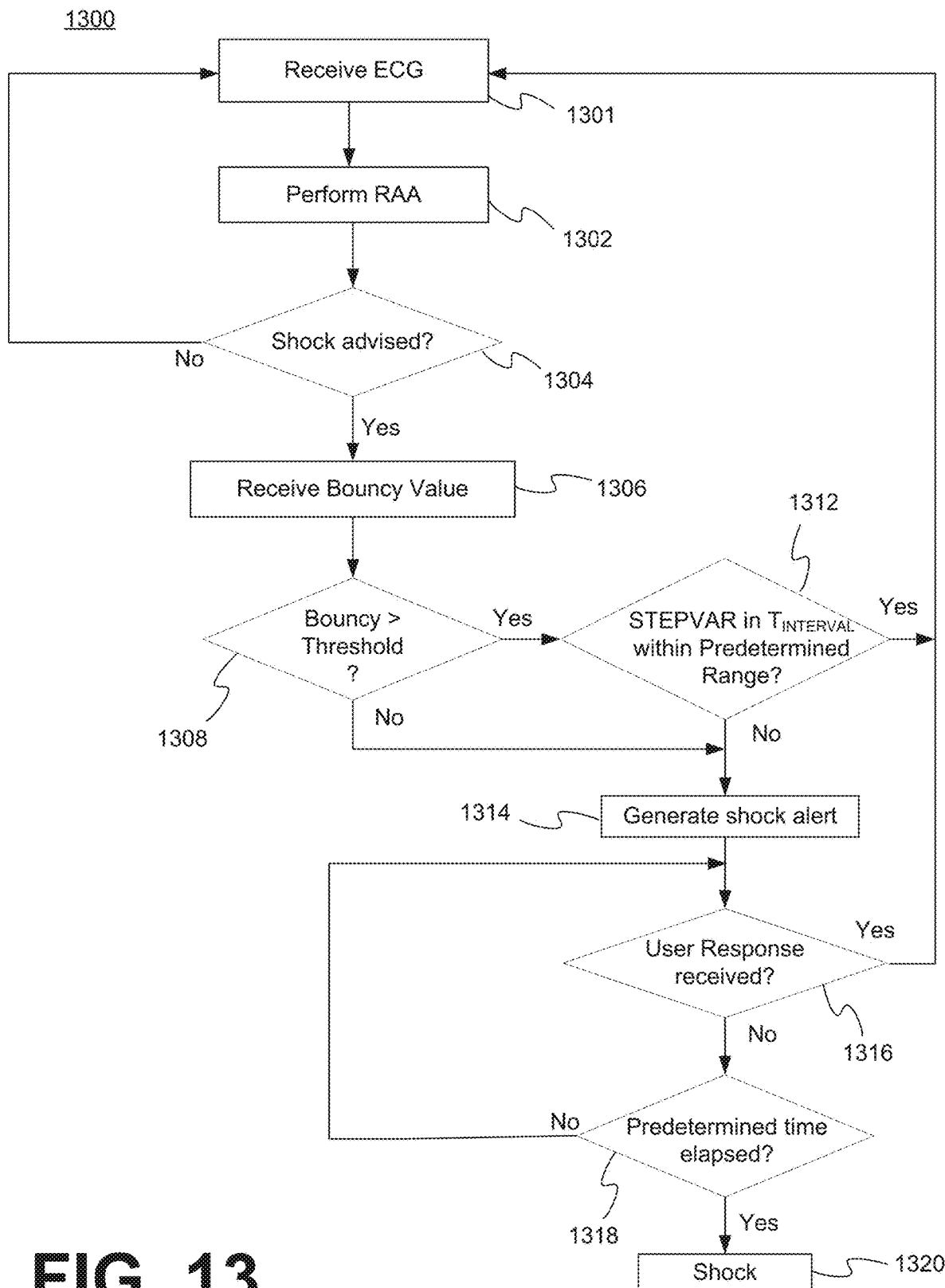
FIG. 13 is an example flow chart illustrating another process for determining whether to provide a shock to a patient, according to embodiments of this disclosure.

FIG. 13 shows an example flow chart illustrating examples of another process 1300 for determining whether to provide a shock to a patient, according to embodiments of this disclosure. Embodiments of process 1300 are substantially similar to the embodiments of process 800 (FIG. 8), but with operation 812 being replaced with an operation 1312. More particularly, embodiments of operations 1301, 1302, 1304, 1306, 1308, 1314, 1316, 1318, and 1320 in FIG. 13 are substantially similar to operations 801, 802, 804, 806, 808, 814, 816, 818, and 820 previously described in conjunction with FIG. 8. Therefore, operation 1312 is described below while the remaining operations of process 1300 are omitted.

As previously described, based on an analysis of Bouncy values in various scenarios, the inventors of the present disclosure have developed algorithms to distinguish between motion due to walking and motion due to transport in a vehicle. For example, in some embodiments according to process 1300, an algorithm uses the analyses that walking generally has a regular or consistent step interval, and thus, can be used to accurately detect waking and to distinguish between walking and transport in a vehicle.

In operation 1312 (performed in response to a determination that the Bouncy value exceeds a Bouncy Threshold in operation 1308), the variability (STEPVAR) of the steps in a preselected time interval is analyzed to determine if STEPVAR falls within one or more preselected ranges indicative of walking or running. Various embodiments for determining STEPVAR are described below. In some embodiments, the preselected time interval is a segment (e.g., about 5 seconds).

If STEPVAR does indicate walking or running, the process 1300 returns to operation 1301 as a shock is not warranted if the patient is walking or running. However, if STEPVAR does not indicate walking or running, then process 1300 proceeds to operation 1314.

One embodiment of determining STEPVAR is as follows. In some patients, the left step interval is not consistent with the right step interval. In some embodiments, the left step interval is compared with the following left step interval and the right step interval is compared with the right step interval. The regularity is measured as the difference of the interval differences. In embodiments, the step interval variability STEPVAR is measured as the average absolute difference of the difference of two step intervals. For example, defining the step intervals as s1, s2, s3 and so on, then for four steps taken in a given preselected time interval STEPVAR is calculated in some embodiments according to equation (3) below:

$$\text{STEPVAR} = \text{average}(\text{abs}((s(i)-s(i+2))-(s(i+1)-s(i+3)))). \quad (3)$$

If the variability is low, operation 1312 is configured to decide or output that the patient is walking or running in that time interval. In some embodiments using equation (3), variability is low when STEPVAR<100 ms, although in other embodiments the threshold can range from 50 ms to 200 ms. Other methods of determining STEPVAR include using the median value, or a mean after excluding "outlier" measurements that are too long or too short. In other embodiments, the potential differences between right and left step intervals are not considered.

Figure 14:
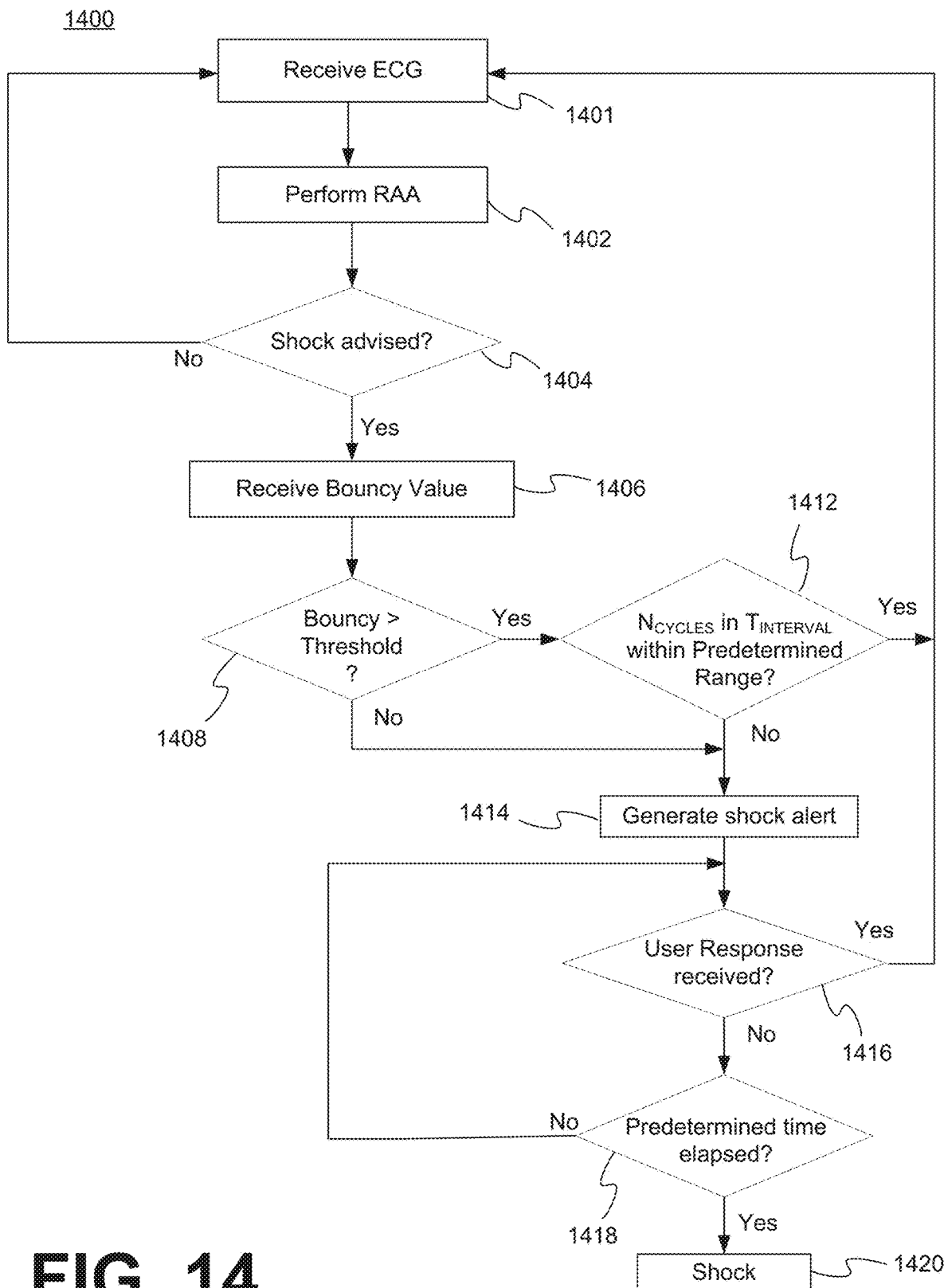
FIG. 14 is an example flow chart illustrating another e process for determining whether to provide a shock to a patient, according to embodiments of this disclosure.

FIG. 14 shows an example flow chart illustrating examples of another process 1400 for determining whether to provide a shock to a patient, according to embodiments of this disclosure. Embodiments of process 1400 are substantially similar to the embodiments of process 800 (FIG. 8), but with operation 812 being replaced with an operation 1412. More particularly, embodiments of operations 1401, 1402, 1404, 1406, 1408, 1414, 1416, 1418, and 1420 in FIG. 14 are substantially similar to operations 801, 802, 804, 806, 808, 814, 816, 818, and 820 previously described in conjunction with FIG. 8. Therefore, operation 1412 is described below while the remaining operations of process 1400 are omitted.

As previously described, based on an analysis of Bouncy values in various scenarios, the inventors of the present disclosure have developed algorithms to distinguish between motion due to walking and motion due to transport in a vehicle. For example, in some embodiments according to process 1400, an algorithm uses the analyses that walking typically generates a motion signal with a morphology that is different from that of a moving vehicle, and thus, can be used to accurately detect waking and to distinguish between walking and transport in a vehicle. One way to characterize the morphology is to count the number of cycles ($N_{CYCLES}$) that occur in a preselected time interval. For example, the algorithm can be configured to detect the number of positive baseline crossings of the motion signal within the preselected time interval. In some embodiments, the motion signal is the Y-axis (or vertical) component of the output signal of a patient-worn accelerometer (e.g., as described above in conjunction with FIG. 3) that has been high pass filtered. In some embodiments the cutoff frequency of the high pass filter is 30 Hz, but can range between 10 Hz and 40 Hz in other embodiments.

In operation 1412 (performed in response to a determination that the Bouncy value exceeds a Bouncy Threshold in operation 1408), the value of $N_{CYCLES}$ in a preselected time interval is analyzed to determine if the value of $N_{CYCLES}$ falls within one or more preselected ranges indicative of walking or running. In some embodiments, the preselected time interval is a segment (e.g., about 5 seconds), and the range indicative of walking/running is <200 cycles. In other embodiments, the range can range from 100 to 200 for a 5 second interval. For embodiments with different preselected time intervals, the range would vary accordingly as can be determined by a person skilled in the art after careful review of this disclosure.

If the value of $N_{CYCLES}$ does indicate walking or running, the process 1400 returns to operation 1401 as a shock is not warranted if the patient is walking or running. However, if the value of $N_{CYCLES}$ does not indicate walking or running, then process 1400 proceeds to operation 1414.

Figure 15:
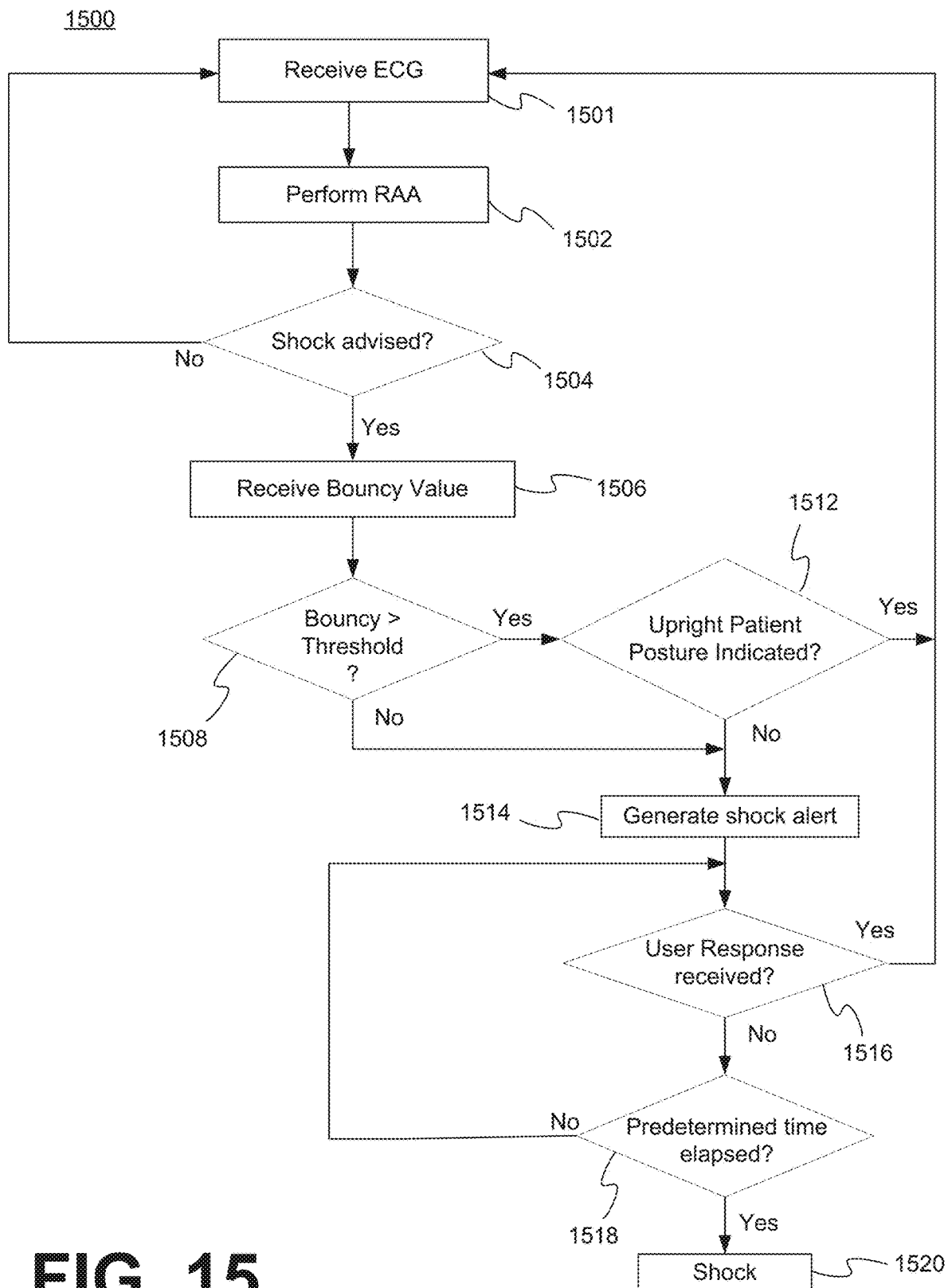
FIG. 15 is an example flow chart illustrating another process for determining whether to provide a shock to a patient, according to embodiments of this disclosure.

FIG. 15 shows an example flow chart illustrating examples of another process 1500 for determining whether to provide a shock to a patient, according to embodiments of this disclosure. Embodiments of process 1500 are substantially similar to the embodiments of process 800 (FIG. 8), but with operation 812 being replaced with an operation 1512. More particularly, embodiments of operations 1501, 1502, 1504, 1506, 1508, 1514, 1516, 1518, and 1520 in FIG. 15 are substantially similar to operations 801, 802, 804, 806, 808, 814, 816, 818, and 820 previously described in conjunction with FIG. 8. Therefore, operation 1512 is described below while the remaining operations of process 1500 are omitted.

As previously described, based on an analysis of Bouncy values in various scenarios, the inventors of the present disclosure have developed algorithms to distinguish between motion due to walking and motion due to transport in a vehicle. For example, in some embodiments according to process 1500, an algorithm uses the analyses that a patient walking typically generates a motion signal that is different from that of a patient in a moving vehicle, and thus, can be used to accurately detect waking and to distinguish between walking and transport in a vehicle. In embodiments of process 1500, the motion sensor signal is used to determine the patient's posture, which is typically different when walking versus sitting in a vehicle. As described above in conjunction with FIGS. 3-6, a patient's posture can be measured using motion sensors such as 3-axis accelerometers. Patients typically have a substantially upright posture while walking and a slightly backward leaning posture when sitting in a vehicle. For example, in some embodiments using 3-axis accelerometer motion detectors, upright posture is determined in response to the Y-axis measurement being less that −0.9 G, and the absolute values of the measurements in the X and Z axes being less than 0.5 G. In other embodiments, the Y-axis threshold can range from −0.85 to −0.95 G, and the X and Z axis thresholds can range from 0.4 to 0.6 G. In some embodiments, while fitting the patient with the system having a walking detector module, the "fitter" or clinician collects posture measurements while the patient is both walking and sitting to determine thresholds used to distinguish between walking and sitting.

In embodiments of operation 1512, if an upright posture for the patient is detected (indicating that the patient is walking or running), the process 1500 returns to operation 1501 as a shock is not warranted. However, if an upright posture is not detected (indicating the patient is not walking or running), then process 1500 proceeds to operation 1514.

In some embodiments, the walking detector module is additionally configured to: (a) turn-off or enter an idle mode when a sitting posture is detected (so that the YES and NO decision paths from operation 1508 go to operations 1501 and 1514, respectively); and (b) turn-on or commence processing when a non-sitting or upright posture is detected.

Figure 16:
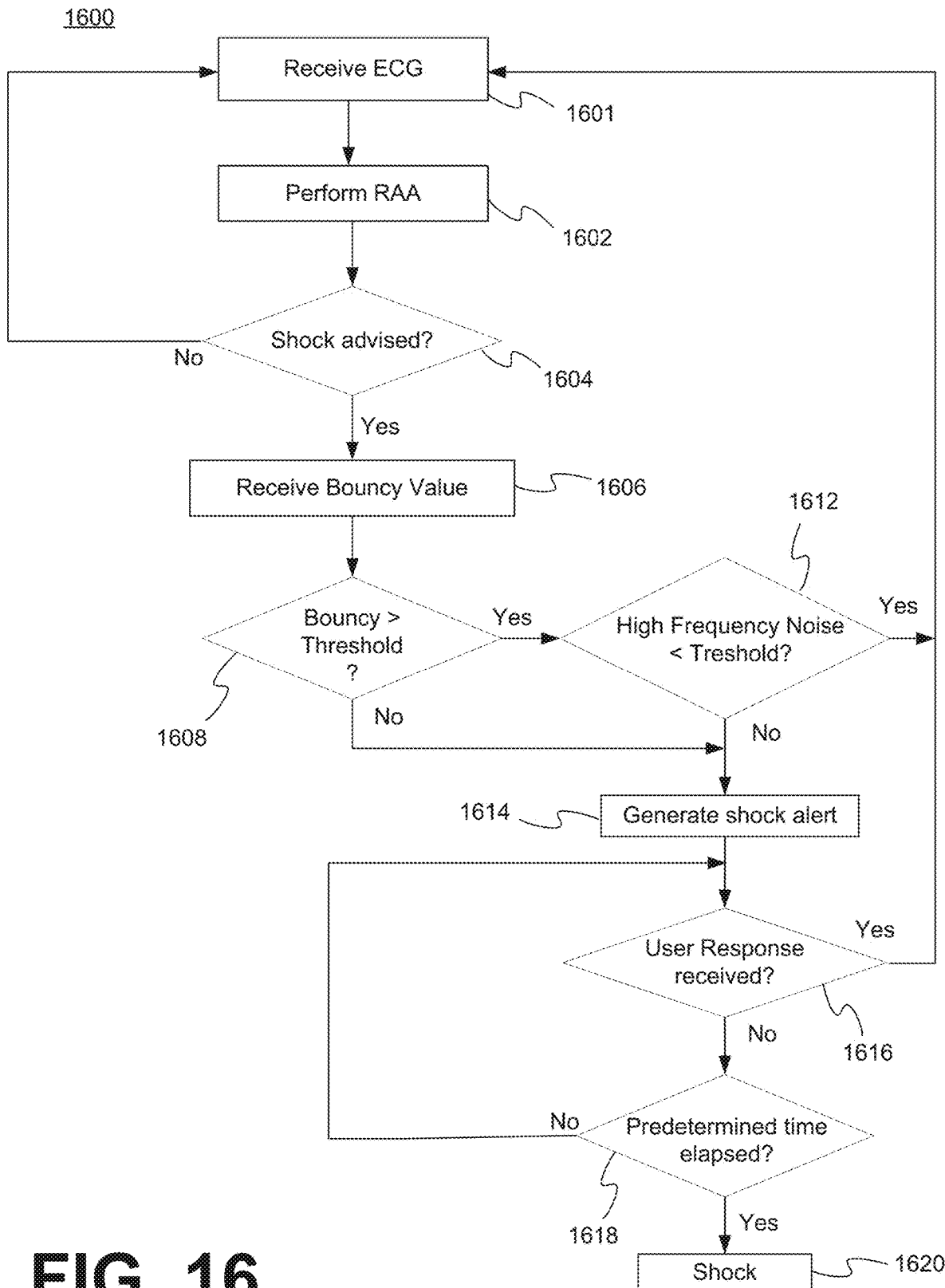
FIG. 16 is an example flow chart illustrating another process for determining whether to provide a shock to a patient, according to embodiments of this disclosure.

FIG. 16 shows an example flow chart illustrating examples of another process 1600 for determining whether to provide a shock to a patient, according to embodiments of this disclosure. Embodiments of process 1600 are substantially similar to the embodiments of process 800 (FIG. 8), but with operation 812 being replaced with an operation 1612. More particularly, embodiments of operations 1601, 1602, 1604, 1606, 1608, 1614, 1616, 1618, and 1620 in FIG. 16 are substantially similar to operations 801, 802, 804, 806, 808, 814, 816, 818, and 820 previously described in conjunction with FIG. 8. Therefore, operation 1612 is described below while the remaining operations of process 1600 are omitted.

As previously described, based on an analysis of Bouncy values in various scenarios, the inventors of the present disclosure have developed algorithms to distinguish between motion due to walking and motion due to transport in a vehicle. In some embodiments of process 1600, the output signal of the motion sensing unit (e.g., motion sensing unit 281A in FIG. 2A) is analyzed for high frequency noise, which is typically different when walking versus sitting in a vehicle.

In some embodiments of operation 1612, the high frequency noise is measured by spectral analysis of the Y axis component of the motion sensor output signal. For example, an FFT can be performed on the signal and the resulting frequency data can be analyzed to determine the level of high frequency noise. In some embodiments, the band above 10 Hz is considered high frequency, and if the magnitude of the acceleration of the high frequency band is greater than a threshold of about 0.5 G the high frequency noise is deemed to be caused by vehicle motion.

In embodiments of operation 1612, if the high frequency noise does exceed the threshold (indicating that the patient is in a vehicle and not walking/running), the process 1600 proceeds to operation 1614. Otherwise, the process 1600 returns to operation 1601 as a shock is not warranted.

Figure 17:
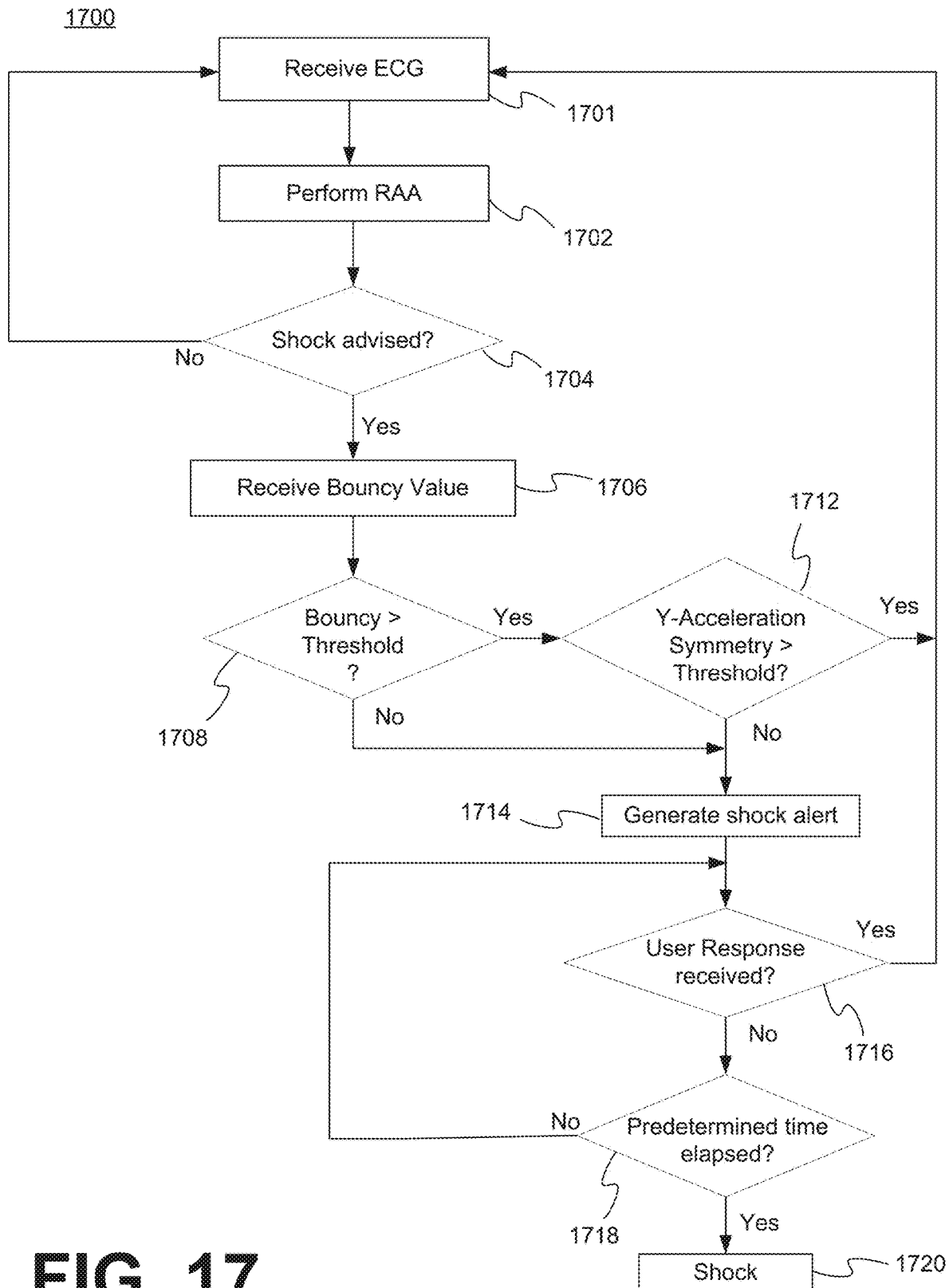
FIG. 17 is example flow chart illustrating another process for determining whether to provide a shock to a patient, according to embodiments of this disclosure.

FIG. 17 shows an example flow chart illustrating examples of another process 1700 for determining whether to provide a shock to a patient, according to embodiments of this disclosure. Embodiments of process 1700 are substantially similar to the embodiments of process 800 (FIG. 8), but with operation 812 being replaced with an operation 1712. More particularly, embodiments of operations 1701, 1702, 1704, 1706, 1708, 1714, 1716, 1718, and 1720 in FIG. 17 are substantially similar to operations 801, 802, 804, 806, 808, 814, 816, 818, and 820 previously described in conjunction with FIG. 8. Therefore, operation 1712 is described below while the remaining operations of process 1700 are omitted.

As previously described, based on an analysis of Bouncy values in various scenarios, the inventors of the present disclosure have developed algorithms to distinguish between motion due to walking and motion due to transport in a vehicle. In some embodiments of process 1700, the motion sensor signal is analyzed for symmetry in the vertical axis direction (i.e., Y-axis), which is typically different when walking versus being transported in a vehicle.

In some embodiments of operation 1712, a motion sensing unit (such as motion sensing unit 281A in FIG. 2A) includes a 3-axis accelerometer. The Y direction component of the motion sensing unit's output signal is analyzed for symmetry. Walking and running are relatively asymmetric in the Y-direction acceleration, while transport in a moving vehicle is symmetric. In some embodiments, the symmetry is measured by the ratio of the positive and negative peak amplitudes.

In embodiments of operation 1712, if the symmetry of the Y-axis acceleration exceeds a preselected symmetry threshold (indicating that the patient is walking/running and not in a vehicle), the process 1700 proceeds to operation 1701 as a shock is not warranted. Otherwise, the process 1700 proceeds to operation 1714. In some embodiments, the symmetry threshold is 0.8, but can range between 0.5 and 0.9 in other embodiments.

Figure 18:
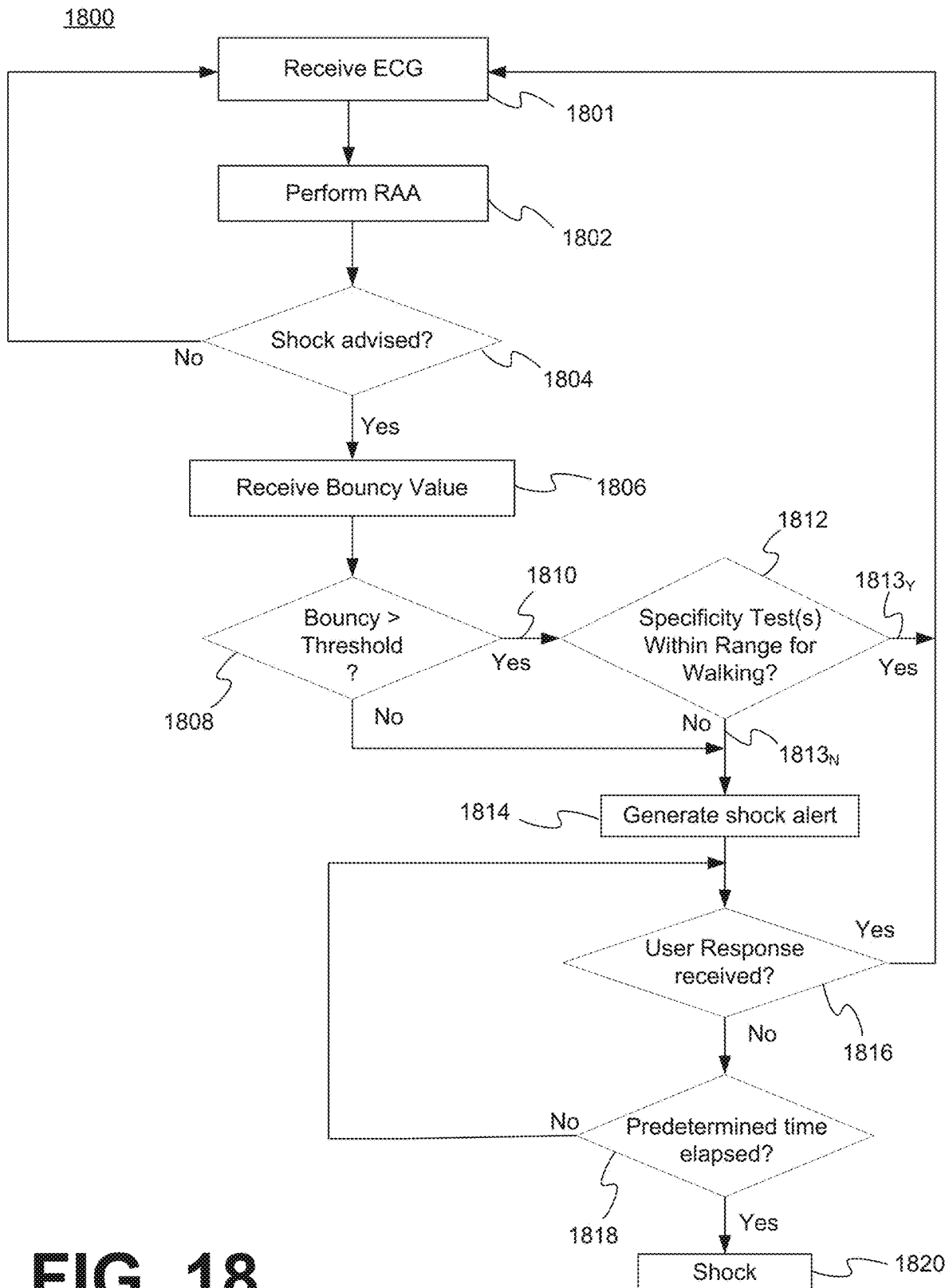
FIG. 18 is an example flow chart illustrating another process for determining whether to provide a shock to a patient, according to embodiments of this disclosure.

FIG. 18 shows an example flow chart illustrating examples of another process 1800 for determining whether to provide a shock to a patient, according to embodiments of this disclosure. Embodiments of process 1800 are substantially similar to the embodiments of process 800 (FIG. 8), but with operation 812 being replaced with an operation 1812. More particularly, embodiments of operations 1801, 1802, 1804, 1806, 1808, 1814, 1816, 1818, and 1820 in FIG. 18 are substantially similar to operations 801, 802, 804, 806, 808, 814, 816, 818, and 820 previously described in conjunction with FIG. 8. Therefore, operation 1812 is described below while the remaining operations of process 1800 are omitted.

As previously described, based on an analysis of Bouncy values in various scenarios, the inventors of the present disclosure have developed algorithms to distinguish between motion due to walking and motion due to transport in a vehicle. In some embodiments of process 1800, one or more specificity tests are applied to the output signal of the motion sensing unit (e.g., motion sensing unit 281A in FIG. 2A). In various embodiments, the specificity tests are substantially similar to operations 1212, 1312, 1412, 1512, 1612 and 1712. Embodiments in which only one specificity test is added, the flow chart will look substantially similar to one of the flow charts of FIGS. 12-17. However, in some embodiments, two or more of the specificity tests are performed sequentially to more accurately detect whether the patient is walking/running.

In some embodiments of operation 1812, a motion sensing unit (such as motion sensing unit 281A in FIG. 2A) includes a 3-axis accelerometer and X, Y and Z axis acceleration signals are provided to a processor such as processor 230 (FIGS. 2, 2A). Embodiments of operation 1812 (FIG. 18) are described below in conjunction with FIG. 19.

Figure 19:
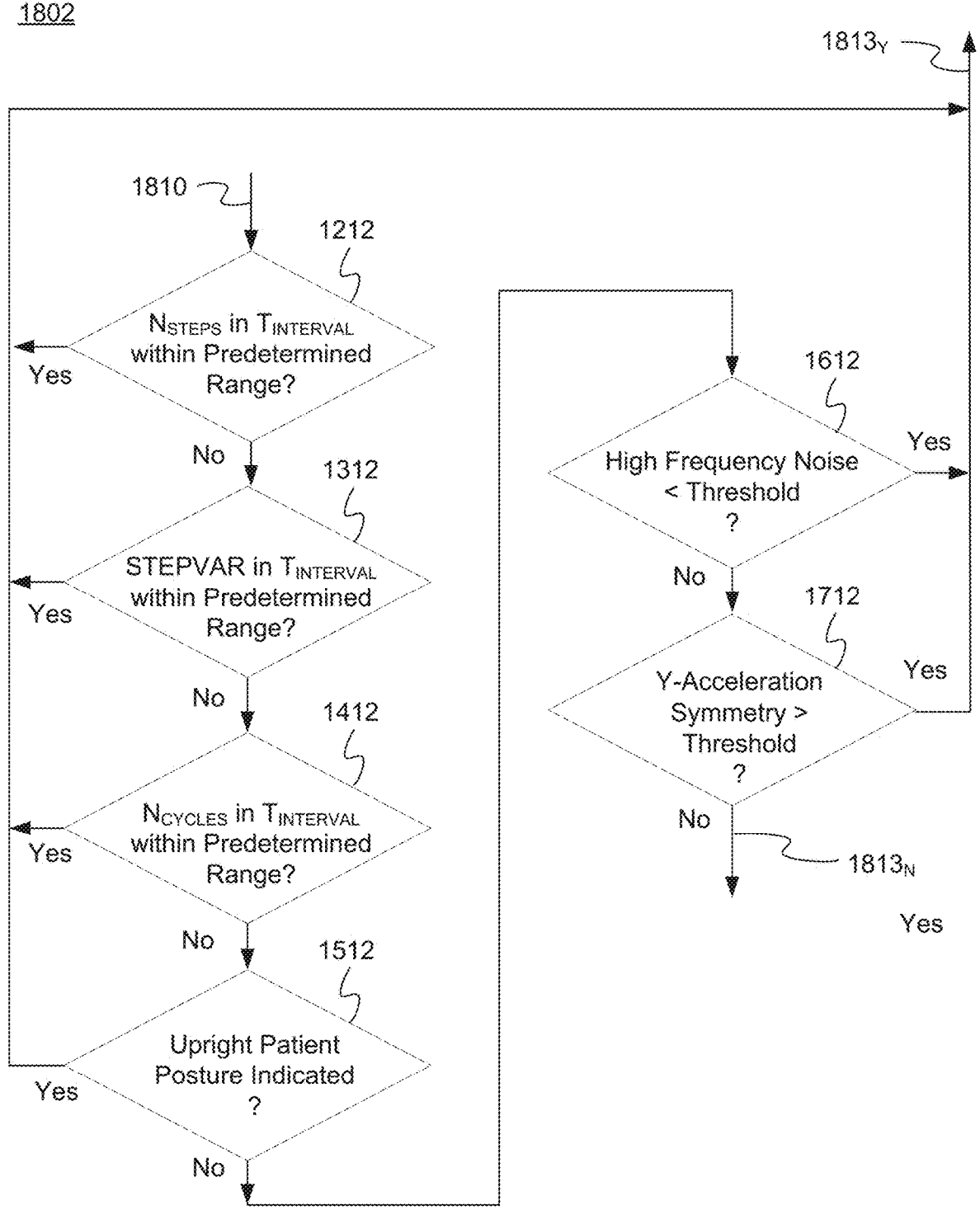
FIG. 19 is an example flow chart illustrating example processes for implementing the specificity test(s) illustrated in FIG. 18, according to embodiments of this disclosure.

In the embodiments of operation 1812 (as shown in FIG. 19), six specificity tests are performed, which are substantially similar to the previously-described operation 1212 (FIG. 12), operation 1312 (FIG. 13), operation 1412 (FIG. 14), operation 1512 (FIG. 15), operation 1612 (FIG. 16), and operation 1712 (FIG. 17). More particularly, when operation 1808 (FIG. 18) indicates that the Bouncy value exceeds a threshold, the process flows as indicated by arrow 1810 in FIGS. 18 and 19 to operation 1212. If operation 121 indicates that the value of $N_{STEPS}$ is within the predetermined range (i.e., indicating walking is detected), in some embodiments the process returns to operation 1801 as indicated by arrow 1813$_Y$. Otherwise, the process flows to operation 1312.

If operation 1312 indicates that the value of STEPVAR is within the predetermined range (i.e., indicating walking is detected), in some embodiment the process returns to operation 1801 as indicated by arrow 1813$_Y$. Otherwise, the process flows to operation 1412.

If operation 1412 indicates that the value of $N_{CYCLES}$ is within the predetermined range (i.e., indicating walking is detected), in some embodiments the process returns to operation 1801 as indicated by arrow 1813$_Y$. Otherwise, the process flows to operation 1512.

If operation 1512 indicates that the patient has an upright posture (i.e., indicating walking is detected), in some embodiments the process returns to operation 1801 as indicated by arrow 1813$_Y$. Otherwise, the process flows to operation 1612.

If operation 1612 indicates that the high frequency noise of the Y direction acceleration is less than the predetermined threshold (i.e., indicating walking is detected), in some embodiments the process returns to operation 1801 as indicated by arrow 1813$_Y$. Otherwise, the process flows to operation 1712.

If operation 1712 indicates that the symmetry of the Y direction acceleration is greater than the predetermined threshold (i.e., indicating walking is detected), in some embodiments the process returns to operation 1801 as indicated by arrow 1813$_Y$. Otherwise, the process flows to operation 1814 as indicated by arrow 1813$_{Y'}$ in FIGS. 18 and 19.

Although FIG. 19 shows operations 1212, 1312, 1412, 1512, 1612, and 1712 performed in a certain order, in other embodiments, these operations are performed in different orders. Further, in some embodiments, one or more of these operations are omitted and/or performed in a different order.

Aspects and examples of the disclosure may operate on particularly created hardware, firmware, digital signal processors, or on a specially programmed computer including a processor operating according to programmed instructions. The terms controller or processor as used herein are intended to include microprocessors, microcomputers, Application Specific Integrated Circuits (ASICs), and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a computer readable storage medium such as a hard disk, optical disk, removable storage media, solid state memory, Random Access Memory (RAM), etc. As will be appreciated by one of skill in the art, the functionality of the program modules may be combined or distributed as desired in various aspects. In addition, the functionality may be embodied in whole or in part in firmware or hardware equivalents such as integrated circuits, field programmable gate arrays (FPGA), and the like. Particular data structures may be used to more effectively implement one or more aspects of the disclosure, and such data structures are contemplated within the scope of computer executable instructions and computer-usable data described herein.

The disclosed aspects and examples may be implemented, in some cases, in hardware, firmware, software, or any combination thereof. The disclosed aspects may also be implemented as instructions carried by or stored on one or more or computer-readable storage media, which may be read and executed by one or more processors. Such instructions may be referred to as a computer program product. Computer-readable media, as discussed herein, means any media that can be accessed by a computing device. By way of example, and not limitation, computer-readable media may comprise computer storage media and communication media.

Computer storage media means any medium that can be used to store computer-readable information. By way of example, and not limitation, computer storage media may include RAM, ROM, Electrically Erasable Programmable Read-Only Memory (EEPROM), flash memory or other memory technology, Compact Disc Read Only Memory (CD-ROM), Digital Video Disc (DVD), or other optical disk storage, magnetic cassettes, magnetic tape, magnetic disk storage or other magnetic storage devices, and any other volatile or nonvolatile, removable or non-removable media implemented in any technology. Computer storage media excludes signals per se and transitory forms of signal transmission.

Communication media means any media that can be used for the communication of computer-readable information. By way of example, and not limitation, communication media may include coaxial cables, fiber-optic cables, air, or any other media suitable for the communication of electrical, optical, Radio Frequency (RF), infrared, acoustic or other types of signals.

Aspects and examples of the present disclosure operate with various modifications and in alternative forms. Specific aspects have been shown by way of example in the drawings and are described in detail herein below. However, it should be noted that the examples disclosed herein are presented for the purposes of clarity of discussion and are not intended to limit the scope of the general concepts disclosed to the specific examples described herein unless expressly limited. As such, the present disclosure is intended to cover all modifications, equivalents, and alternatives of the described aspects in light of the attached drawings and claims.

References in the specification to embodiment, aspect, example, etc., indicate that the described item may include a particular feature, structure, or characteristic. However, every disclosed aspect may or may not necessarily include that particular feature, structure, or characteristic. Moreover, such phrases are not necessarily referring to the same aspect unless specifically noted. Further, when a particular feature, structure, or characteristic is described regarding a particular aspect, such feature, structure, or characteristic can be employed in connection with another disclosed aspect whether or not such feature is explicitly described in conjunction with such other disclosed aspect.

The previously described versions of the disclosed subject matter have many advantages that were either described or would be apparent to a person of ordinary skill. Even so, these advantages or features are not required in all versions of the disclosed apparatus, systems, or methods.

Additionally, this written description makes reference to particular features. It is to be understood that the disclosure in this specification includes all possible combinations of those particular features. Where a particular feature is disclosed in the context of a particular aspect or example, that feature can also be used, to the extent possible, in the context of other aspects and examples.

Also, when reference is made in this application to a method having two or more defined steps or operations, the defined steps or operations can be carried out in any order or simultaneously, unless the context excludes those possibilities.

Although specific examples of the disclosure have been illustrated and described for purposes of illustration, it will be understood that after careful review of the present disclosure one skilled in art may make various modifications without departing from the spirit and scope of the disclosure. Accordingly, the disclosure should not be limited except as by the appended claims.

What is claimed is:

1. A wearable cardioverter defibrillator (WCD), comprising:
   a support structure configured to be worn by an ambulatory patient;
   an energy storage module configured to store an electrical charge;
   a discharge circuit coupled to the energy storage module;
   electrodes configured to render an electrocardiogram (ECG) signal of the patient while the ambulatory patient is wearing the support structure;
   a motion sensor configured to output one or more signals indicative of an acceleration of the ambulatory patient in a vertical direction while the ambulatory patient is wearing the support structure; and a processor configured to:
receive the one or more signals from the motion sensor, receive the ECG signal,
determine from the ECG signal whether a shock criterion is met;
responsive to the shock criterion being met, perform one or more tests on the one or more signals received from the motion sensor to determine if the patient is walking or running, wherein at least one of the one or more tests being based on a parameter derived at least in part from an AC component of the patient's acceleration in the vertical direction,
responsive to a determination that the patient is not walking or running, cause the discharge circuit to discharge the stored electrical charge, and
responsive to a determination that the patient is walking or running, inhibit the discharge circuit from discharging the stored electrical charge.

2. The WCD of claim 1, wherein the parameter is derived at least in part of the Fast Fourier Transform (FFT) of the AC component of the patient's acceleration in the vertical direction.

3. The WCD of claim 1, wherein the test based on the parameter comprises comparing the parameter to a predetermined threshold to determine whether or not the patient's movement meets a first criterion indictive of walking.

4. The WCD of claim 1, wherein the one or more tests include at least one specificity test that is conducted after the test based on the parameter determines the patient meets a first criterion indictive of walking, the at least one specificity test to determine if the patient's movement meets a second criterion indictive of walking.

5. The WCD of claim 4, wherein the one or more specificity tests comprises at least two specificity tests.

6. The WCD of claim 4, further comprising a step detector and wherein a specificity test is based on a number of steps detected during a predetermined time interval.

7. The WCD of claim 4, further comprising a step detector and wherein a specificity test is based on a variability of steps determined for steps detected in a predetermined time interval.

8. The WCD of claim 4, wherein a specificity test is based on a number of cycles in the one or more signals from the motion sensor detected in a predetermined time interval.

9. The WCD of claim 4, wherein a specificity test is based on a level of noise detected above 10 Hz in the one or more signals from the motion sensor during a predetermined time interval.

10. The WCD of claim 4, wherein a specificity test is based on a symmetry of the patient's acceleration in the vertical direction measured in a predetermined time interval.

11. The WCD of claim 1, further comprising a step detector configured to detect a step after a peak is detected in the acceleration in the vertical direction by comparing an acceleration measurement in the vertical direction taken at a known time after the detected peak with a threshold having a value corresponding to the known time, wherein the threshold's value is initially set to the detected peak's value and, after a predetermined refractory period after the peak was detected, exponentially decays toward a predetermined minimum value.

* * * * *

UNITED STATES PATENT AND TRADEMARK OFFICE
CERTIFICATE OF CORRECTION

PATENT NO. : 11,400,303 B2
APPLICATION NO. : 16/158174
DATED : August 2, 2022
INVENTOR(S) : Jaeho Kim, Joseph L. Sullivan and Robert P. Marx Page 1 of 1

It is certified that error appears in the above-identified patent and that said Letters Patent is hereby corrected as shown below:

On the Title Page

Item (63), Related U.S. Application Data, please delete "Continuation-in-part of application No. 15/863,551, filed on Jan. 5, 2018, now Pat. No. 11,083,906" and replace with
--Continuation-in-part of application No. 15/863,551, filed on Jan. 5, 2018, now Pat. No. 11,083,906, which claims benefit of provisional application No. 62/442,925, filed Jan. 5, 2017 and provisional application No. 62/446,820, filed Jan. 16, 2017."--

Signed and Sealed this
Eighth Day of April, 2025

Coke Morgan Stewart
*Acting Director of the United States Patent and Trademark Office*